United States Patent
Petrou

(10) Patent No.: US 11,939,582 B2
(45) Date of Patent: Mar. 26, 2024

(54) ANTISENSE OLIGONUCLEOTIDES TARGETING SCN2A FOR THE TREATMENT OF SCN1A ENCEPHALOPATHIES

(71) Applicant: RogCon, Inc., Miami Beach, FL (US)

(72) Inventor: Steven Petrou, Eltham (AU)

(73) Assignee: RogCon, Inc., Miami Beach, FL (US)

( * ) Notice: Subject to any disclaimer, the term of this patent is extended or adjusted under 35 U.S.C. 154(b) by 0 days.

(21) Appl. No.: 17/269,706

(22) PCT Filed: Aug. 20, 2019

(86) PCT No.: PCT/US2019/047313
§ 371 (c)(1),
(2) Date: Feb. 19, 2021

(87) PCT Pub. No.: WO2020/041348
PCT Pub. Date: Feb. 27, 2020

(65) Prior Publication Data
US 2021/0317462 A1    Oct. 14, 2021

Related U.S. Application Data

(60) Provisional application No. 62/765,344, filed on Aug. 20, 2018.

(51) Int. Cl.
| | | |
|---|---|---|
| C12N 15/11 | (2006.01) | |
| A61K 9/00 | (2006.01) | |
| A61P 25/00 | (2006.01) | |
| C12N 15/113 | (2010.01) | |

(52) U.S. Cl.
CPC ........ *C12N 15/1138* (2013.01); *A61K 9/0085* (2013.01); *A61P 25/00* (2018.01); *C12N 2310/11* (2013.01); *C12N 2310/314* (2013.01); *C12N 2310/321* (2013.01); *C12N 2310/322* (2013.01); *C12N 2310/3233* (2013.01); *C12N 2310/3341* (2013.01); *C12N 2310/341* (2013.01); *C12N 2310/346* (2013.01); *C12N 2320/32* (2013.01)

(58) Field of Classification Search
CPC ............ C12N 15/1138; C12N 2310/11; C12N 2310/321; C12N 2310/322; C12N 2310/341
See application file for complete search history.

(56) References Cited

U.S. PATENT DOCUMENTS

| | | |
|---|---|---|
| 7,803,930 B2 | 9/2010 | Crooke et al. |
| 9,771,579 B2 | 9/2017 | Collard et al. |
| 2006/0088827 A1 | 4/2006 | Hipfel et al. |
| 2010/0088778 A1 | 4/2010 | Mulley et al. |
| 2011/0294155 A1 | 12/2011 | Petrou et al. |
| 2013/0096183 A1 | 4/2013 | Collard |
| 2015/0315579 A1 | 11/2015 | Bhat et al. |
| 2017/0044540 A1 | 2/2017 | Saetrom et al. |
| 2017/0240904 A1 | 8/2017 | Tallent et al. |
| 2017/0355990 A1 | 12/2017 | Collard et al. |
| 2018/0002696 A1 | 1/2018 | Collard et al. |
| 2018/0362987 A1 | 12/2018 | Krainer et al. |
| 2018/0369275 A1 | 12/2018 | Arnarez et al. |

FOREIGN PATENT DOCUMENTS

| | | | |
|---|---|---|---|
| WO | WO-2004016754 A2 * | 2/2004 | ......... C12N 15/1138 |
| WO | 2015109034 A1 | 7/2015 | |
| WO | 2015193651 A1 | 12/2015 | |
| WO | 2016054615 A2 | 4/2016 | |
| WO | 2017106377 A1 | 6/2017 | |
| WO | 2017106382 A1 | 6/2017 | |
| WO | 2018064498 A1 | 4/2018 | |
| WO | 2018098499 A1 | 5/2018 | |
| WO | 2019028440 A1 | 2/2019 | |
| WO | 2019040923 A1 | 2/2019 | |
| WO | 2019232209 A1 | 12/2019 | |

OTHER PUBLICATIONS

Ogiwara et al., Nav1.1 Localizes to Axons of Parvalbumin-Positive Inhibitory Interneurons: A Circuit Basis for Epileptic Seizures in Mice Carrying an Scn1a Gene Mutation, The Journal of Neuroscience, 2007, 27(22):5903-5914 (Year: 2007).*

NCBI accession No. NM_001353955.2 (GenBank, 2007, pp. 1-13). (Year: 2007).*

Whittmann-Regis, Agnes (Authorized officer), International Preliminary Report on Patentability for corresponding International Patent Application No. PCT/US2019/047313, dated Feb. 23, 2021 (7 pages).

Young, Lee (Authorized officer), International Search Report and Written Opinion for corresponding International Patent Application No. PCT/US2019/047313, dated Dec. 19, 2019 (11 pages).

Maljevic et al., Models for discovery of targeted therapy in generic epileptic encephalopathies, J. Neurochem. 2017, vol. 143(1), p. 30-48.

NCBI Accession No. NM_021007.2, *Homo sapiens* sodium voltage-gates channel alpha subunit 2 (SCN2A), transcript variant 1, mRNA. Jul. 21, 2018. [online]. Retrieved from the Internet on Apr. 14, 2022 from www.ncbi.nlm.nih.gov/nuccore/93141209?sat=46&satkey=166483782.

Baumer et al., SCN2A-Related Early-Onset Epileptic Encephalopathy Responsive to Phenobarbital. J. Pediatr. Epilepsy., 2016, vol. 5(1), p. 42-46.

Young, Lee (Authorized Officer), International Search Report and Written Opinion dated Apr. 6, 2021 in corresponding International Application No. PCT/US2020/062317, 14 pages.

(Continued)

*Primary Examiner* — Ekaterina Poliakova-Georgantas
(74) *Attorney, Agent, or Firm* — McCarter & English, LLP; Jonathan M. Sparks; Yelena Margolin

(57) ABSTRACT

Provided herein are methods, compounds, and compositions for reducing expression of sodium voltage-gated channel alpha subunit 2 (SCN2A) in a subject. Such methods, compounds, and compositions are useful to treat, prevent, delay, or ameliorate a sodium voltage gated channel alpha subunit 1 (SCN1A) related disease or disorder (e.g., Dravet syndrome) in a subject in need.

14 Claims, 5 Drawing Sheets
Specification includes a Sequence Listing.

(56) References Cited

OTHER PUBLICATIONS

"Flynn et al. ""Correlation and Prediction of Mass Transport across Membranes I: Influence of Alkyl Chain Length on Flux-Determining Properties of Barrier and Diffusant""", Journal of Pharmaceutical Sciences. 1972. vol. 61(6), pp. 838-852, especially: p. 843, col. 2, para 2."

Berecki et al., "Dynamic action potential clamp predicts functional separation in mild familial and sever de novo forms of SCN2A epilepsy," Proc Natl Acad Sci U.S.A. 115(24): E5516-E5525 (2018).

International Search Report and Written Opinion for International Patent Application No. PCT/US2019/014030, dated May 3, 2019 (9 pages).

International Search Report and Written Opinion for International Patent Application No. PCT/US2019/034171, dated Aug. 27, 2019 (10 pages).

Office Action issued in U.S. Appl. No. 16/533,112 dated Feb. 3, 2021, 12 pages.

Vasylyev et al. "Dynamic-clamp analysis of wild-type human Nav1.7 and erythromelalgia mutant channel L858H," J Neurophysiol. 111(7):1429-43 (2014).

International Search Report and Written Opinion for International Patent Application No. PCT/US2020/014714, dated Apr. 1, 2020 (9 pages).

Kole et al., "RNA therapeutics: beyond RNA interference and antisense oligonucleotides," Nat Rev Drug Discov. 11(2):125-40 (2012).

Berret et al., "Oligodendrogial excitability mediated by glutamatergic inputs and Nav1.2 activation", Nature Communications, vol. 8, No. 1, Dec. 1, 2017 (Dec. 1, 2017), XP055917371, DOI: 10.1038/s41467-017-00688-0 Retrieved from the Internet: URL:https://www.nature.com/articles/s41467-017-00688-0.pdf.

Xiang et al., "Regulation of Cu—Zn superoxide dismutase on SCN2A in SH-SY5Y cells as a potential therapy for temporal lobe epilepsy", Molecular Medicine Reports, vol. 9, No. 1, Nov. 11, 2013 (Nov. 11, 2013), pp. 16-22, XP055909901, GR ISSN: 1791-2997, DOI: 10.3892/mmr.2013.1790.

Makinson et al., "Role of the hippocampus in Nav1.6 (Scn8a) mediated seizure resistance", Neurobiology of Disease, vol. 68, pp. 16-25, XP028855714, ISSN: 0969-9961, DOI: 10.1016/J.NBD.2014.03.014.

European Search Report issued in European Patent Application No. 19851888.8 dated Jun. 17, 2022, 9 pages.

Shi et al., "Missense mutation of the sodium channel gene SCN2A causes Dravet syndrome", Brain & Development, 2009, vol. 31, pp. 758-762.

Duménieu et al., "The Segregated Expression of Voltage-Gated Potassium and Sodium Channels in Neuronal Membranes: Functional Implications and Regulatory Mechanisms", Frontiers in Cellular Neuroscience, Apr. 24, 2017, 19 pages.

\* cited by examiner

```
                        SEQUENCE LISTING

<160> NUMBER OF SEQ ID NOS: 12

<210> SEQ ID NO 1
<211> LENGTH: 16
<212> TYPE: DNA
<213> ORGANISM: Artificial Sequence
<220> FEATURE:
<223> OTHER INFORMATION: Synthetic Construct

<400> SEQUENCE: 1
aaagctaaga gaccca                                                        16

<210> SEQ ID NO 2
<211> LENGTH: 16
<212> TYPE: DNA
<213> ORGANISM: Artificial Sequence
<220> FEATURE:
<223> OTHER INFORMATION: Synthetic Construct

<400> SEQUENCE: 2
agattgcatt ttcacc                                                        16

<210> SEQ ID NO 3
<211> LENGTH: 16
<212> TYPE: DNA
<213> ORGANISM: Artificial Sequence
<220> FEATURE:
<223> OTHER INFORMATION: Synthetic Construct

<400> SEQUENCE: 3
ggcaatactt cccaac                                                        16

<210> SEQ ID NO 4
<211> LENGTH: 16
<212> TYPE: DNA
<213> ORGANISM: Artificial Sequence
<220> FEATURE:
<223> OTHER INFORMATION: Synthetic Construct

<400> SEQUENCE: 4
tgggtctctt agcttt                                                        16

<210> SEQ ID NO 5
<211> LENGTH: 16
<212> TYPE: DNA
<213> ORGANISM: Artificial Sequence
<220> FEATURE:
<223> OTHER INFORMATION: Synthetic Construct

<400> SEQUENCE: 5
ggtgaaaatg caatct                                                        16

<210> SEQ ID NO 6
<211> LENGTH: 16
```

```
<212> TYPE: DNA
<213> ORGANISM: Artificial Sequence
<220> FEATURE:
<223> OTHER INFORMATION: Synthetic Construct

<400> SEQUENCE: 6
gttgggaagt attgcc                                                          16

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
tgctgtgcgg aaatctgcc                                                       19

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
cggatgctca agagagactg g                                                    21

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
gaggtgctgc tgatgtgc                                                        18

<210> SEQ ID NO 10
<211> LENGTH: 19
<212> TYPE: DNA
<213> ORGANISM: Artificial Sequence
<220> FEATURE:
<223> OTHER INFORMATION: Synthetic Construct

<400> SEQUENCE: 10
ggcgttggga ttggtgact                                                       19

<210> SEQ ID NO 11
<211> LENGTH: 2005
<212> TYPE: PRT
<213> ORGANISM: Homo sapiens
<220> FEATURE:
<221> NAME/KEY: MISC_FEATURE
<223> OTHER INFORMATION: NP_066287.2

<400> SEQUENCE: 11

Met Ala Gln Ser Val Leu Val Pro Pro Gly Pro Asp Ser Phe Arg Phe
1               5                   10                  15

Phe Thr Arg Glu Ser Leu Ala Ala Ile Glu Gln Arg Ile Ala Glu Glu
                20                  25                  30

Lys Ala Lys Arg Pro Lys Gln Glu Arg Lys Asp Glu Asp Asp Glu Asn
            35                  40                  45

Gly Pro Lys Pro Asn Ser Asp Leu Glu Ala Gly Lys Ser Leu Pro Phe
        50                  55                  60
```

```
Ile Tyr Gly Asp Ile Pro Pro Glu Met Val Ser Val Pro Leu Glu Asp
 65                  70                  75                  80

Leu Asp Pro Tyr Tyr Ile Asn Lys Lys Thr Phe Ile Val Leu Asn Lys
                 85                  90                  95

Gly Lys Ala Ile Ser Arg Phe Ser Ala Thr Pro Ala Leu Tyr Ile Leu
            100                 105                 110

Thr Pro Phe Asn Pro Ile Arg Lys Leu Ala Ile Lys Ile Leu Val His
            115                 120                 125

Ser Leu Phe Asn Met Leu Ile Met Cys Thr Ile Leu Thr Asn Cys Val
130                 135                 140

Phe Met Thr Met Ser Asn Pro Pro Asp Trp Thr Lys Asn Val Glu Tyr
145                 150                 155                 160

Thr Phe Thr Gly Ile Tyr Thr Phe Glu Ser Leu Ile Lys Ile Leu Ala
                165                 170                 175

Arg Gly Phe Cys Leu Glu Asp Phe Thr Phe Leu Arg Asp Pro Trp Asn
            180                 185                 190

Trp Leu Asp Phe Thr Val Ile Thr Phe Ala Tyr Val Thr Glu Phe Val
            195                 200                 205

Asp Leu Gly Asn Val Ser Ala Leu Arg Thr Phe Arg Val Leu Arg Ala
210                 215                 220

Leu Lys Thr Ile Ser Val Ile Pro Gly Leu Lys Thr Ile Val Gly Ala
225                 230                 235                 240

Leu Ile Gln Ser Val Lys Lys Leu Ser Asp Val Met Ile Leu Thr Val
                245                 250                 255

Phe Cys Leu Ser Val Phe Ala Leu Ile Gly Leu Gln Leu Phe Met Gly
            260                 265                 270

Asn Leu Arg Asn Lys Cys Leu Gln Trp Pro Pro Asp Asn Ser Ser Phe
            275                 280                 285

Glu Ile Asn Ile Thr Ser Phe Phe Asn Asn Ser Leu Asp Gly Asn Gly
290                 295                 300

Thr Thr Phe Asn Arg Thr Val Ser Ile Phe Asn Trp Asp Glu Tyr Ile
305                 310                 315                 320

Glu Asp Lys Ser His Phe Tyr Phe Leu Glu Gly Gln Asn Asp Ala Leu
                325                 330                 335

Leu Cys Gly Asn Ser Ser Asp Ala Gly Gln Cys Pro Glu Gly Tyr Ile
            340                 345                 350

Cys Val Lys Ala Gly Arg Asn Pro Asn Tyr Gly Tyr Thr Ser Phe Asp
            355                 360                 365

Thr Phe Ser Trp Ala Phe Leu Ser Leu Phe Arg Leu Met Thr Gln Asp
370                 375                 380

Phe Trp Glu Asn Leu Tyr Gln Leu Thr Leu Arg Ala Ala Gly Lys Thr
385                 390                 395                 400

Tyr Met Ile Phe Phe Val Leu Val Ile Phe Leu Gly Ser Phe Tyr Leu
                405                 410                 415

Ile Asn Leu Ile Leu Ala Val Val Ala Met Ala Tyr Glu Glu Gln Asn
            420                 425                 430

Gln Ala Thr Leu Glu Glu Ala Glu Gln Lys Glu Ala Glu Phe Gln Gln
            435                 440                 445

Met Leu Glu Gln Leu Lys Lys Gln Gln Glu Glu Ala Gln Ala Ala Ala
            450                 455                 460

Ala Ala Ala Ser Ala Glu Ser Arg Asp Phe Ser Gly Ala Gly Gly Ile
465                 470                 475                 480
```

-continued

```
Gly Val Phe Ser Glu Ser Ser Val Ala Ser Lys Leu Ser Ser Lys
                485                 490                 495

Ser Glu Lys Glu Leu Lys Asn Arg Arg Lys Lys Lys Gln Lys Glu
            500                 505                 510

Gln Ser Gly Glu Glu Lys Asn Asp Arg Val Arg Lys Ser Glu Ser
        515                 520                 525

Glu Asp Ser Ile Arg Arg Lys Gly Phe Arg Phe Ser Leu Glu Gly Ser
    530                 535                 540

Arg Leu Thr Tyr Glu Lys Arg Phe Ser Pro His Gln Ser Leu Leu
545                 550                 555                 560

Ser Ile Arg Gly Ser Leu Phe Ser Pro Arg Arg Asn Ser Arg Ala Ser
                565                 570                 575

Leu Phe Ser Phe Arg Gly Arg Ala Lys Asp Ile Gly Ser Glu Asn Asp
            580                 585                 590

Phe Ala Asp Asp Glu His Ser Thr Phe Glu Asp Asn Asp Ser Arg Arg
        595                 600                 605

Asp Ser Leu Phe Val Pro His Arg His Gly Glu Arg Arg His Ser Asn
    610                 615                 620

Val Ser Gln Ala Ser Arg Ala Ser Arg Val Leu Pro Ile Leu Pro Met
625                 630                 635                 640

Asn Gly Lys Met His Ser Ala Val Asp Cys Asn Gly Val Val Ser Leu
                645                 650                 655

Val Gly Gly Pro Ser Thr Leu Thr Ser Ala Gly Gln Leu Leu Pro Glu
            660                 665                 670

Gly Thr Thr Thr Glu Thr Glu Ile Arg Lys Arg Arg Ser Ser Ser Tyr
        675                 680                 685

His Val Ser Met Asp Leu Leu Glu Asp Pro Thr Ser Arg Gln Arg Ala
    690                 695                 700

Met Ser Ile Ala Ser Ile Leu Thr Asn Thr Met Glu Glu Leu Glu Glu
705                 710                 715                 720

Ser Arg Gln Lys Cys Pro Pro Cys Trp Tyr Lys Phe Ala Asn Met Cys
                725                 730                 735

Leu Ile Trp Asp Cys Cys Lys Pro Trp Leu Lys Val Lys His Leu Val
            740                 745                 750

Asn Leu Val Val Met Asp Pro Phe Val Asp Leu Ala Ile Thr Ile Cys
        755                 760                 765

Ile Val Leu Asn Thr Leu Phe Met Ala Met Glu His Tyr Pro Met Thr
    770                 775                 780

Glu Gln Phe Ser Ser Val Leu Ser Val Gly Asn Leu Val Phe Thr Gly
785                 790                 795                 800

Ile Phe Thr Ala Glu Met Phe Leu Lys Ile Ile Ala Met Asp Pro Tyr
                805                 810                 815

Tyr Tyr Phe Gln Glu Gly Trp Asn Ile Phe Asp Gly Phe Ile Val Ser
            820                 825                 830

Leu Ser Leu Met Glu Leu Gly Leu Ala Asn Val Glu Gly Leu Ser Val
        835                 840                 845

Leu Arg Ser Phe Arg Leu Leu Arg Val Phe Lys Leu Ala Lys Ser Trp
    850                 855                 860

Pro Thr Leu Asn Met Leu Ile Lys Ile Ile Gly Asn Ser Val Gly Ala
865                 870                 875                 880

Leu Gly Asn Leu Thr Leu Val Leu Ala Ile Ile Val Phe Ile Phe Ala
                885                 890                 895

Val Val Gly Met Gln Leu Phe Gly Lys Ser Tyr Lys Glu Cys Val Cys
```

```
                900             905             910
Lys Ile Ser Asn Asp Cys Glu Leu Pro Arg Trp His Met His Asp Phe
        915             920             925
Phe His Ser Phe Leu Ile Val Phe Arg Val Leu Cys Gly Glu Trp Ile
        930             935             940
Glu Thr Met Trp Asp Cys Met Glu Val Ala Gly Gln Thr Met Cys Leu
945             950             955             960
Thr Val Phe Met Met Val Met Val Ile Gly Asn Leu Val Val Leu Asn
                965             970             975
Leu Phe Leu Ala Leu Leu Leu Ser Ser Phe Ser Ser Asp Asn Leu Ala
                980             985             990
Ala Thr Asp Asp Asp Asn Glu Met Asn Asn Leu Gln Ile Ala Val Gly
        995             1000            1005
Arg Met Gln Lys Gly Ile Asp Phe Val Lys Arg Lys Ile Arg Glu
    1010            1015            1020
Phe Ile Gln Lys Ala Phe Val Arg Lys Gln Lys Ala Leu Asp Glu
    1025            1030            1035
Ile Lys Pro Leu Glu Asp Leu Asn Asn Lys Lys Asp Ser Cys Ile
    1040            1045            1050
Ser Asn His Thr Thr Ile Glu Ile Gly Lys Asp Leu Asn Tyr Leu
    1055            1060            1065
Lys Asp Gly Asn Gly Thr Thr Ser Gly Ile Gly Ser Ser Val Glu
    1070            1075            1080
Lys Tyr Val Val Asp Glu Ser Asp Tyr Met Ser Phe Ile Asn Asn
    1085            1090            1095
Pro Ser Leu Thr Val Thr Val Pro Ile Ala Val Gly Glu Ser Asp
    1100            1105            1110
Phe Glu Asn Leu Asn Thr Glu Glu Phe Ser Glu Ser Asp Met
    1115            1120            1125
Glu Glu Ser Lys Glu Lys Leu Asn Ala Thr Ser Ser Ser Glu Gly
    1130            1135            1140
Ser Thr Val Asp Ile Gly Ala Pro Ala Glu Gly Glu Gln Pro Glu
    1145            1150            1155
Val Glu Pro Glu Glu Ser Leu Glu Pro Glu Ala Cys Phe Thr Glu
    1160            1165            1170
Asp Cys Val Arg Lys Phe Lys Cys Cys Gln Ile Ser Ile Glu Glu
    1175            1180            1185
Gly Lys Gly Lys Leu Trp Trp Asn Leu Arg Lys Thr Cys Tyr Lys
    1190            1195            1200
Ile Val Glu His Asn Trp Phe Glu Thr Phe Ile Val Phe Met Ile
    1205            1210            1215
Leu Leu Ser Ser Gly Ala Leu Ala Phe Glu Asp Ile Tyr Ile Glu
    1220            1225            1230
Gln Arg Lys Thr Ile Lys Thr Met Leu Glu Tyr Ala Asp Lys Val
    1235            1240            1245
Phe Thr Tyr Ile Phe Ile Leu Glu Met Leu Leu Lys Trp Val Ala
    1250            1255            1260
Tyr Gly Phe Gln Val Tyr Phe Thr Asn Ala Trp Cys Trp Leu Asp
    1265            1270            1275
Phe Leu Ile Val Asp Val Ser Leu Val Ser Leu Thr Ala Asn Ala
    1280            1285            1290
Leu Gly Tyr Ser Glu Leu Gly Ala Ile Lys Ser Leu Arg Thr Leu
    1295            1300            1305
```

```
Arg Ala Leu Arg Pro Leu Arg Ala Leu Ser Arg Phe Glu Gly Met
    1310                1315                1320

Arg Val Val Val Asn Ala Leu Leu Gly Ala Ile Pro Ser Ile Met
    1325                1330                1335

Asn Val Leu Leu Val Cys Leu Ile Phe Trp Leu Ile Phe Ser Ile
    1340                1345                1350

Met Gly Val Asn Leu Phe Ala Gly Lys Phe Tyr His Cys Ile Asn
    1355                1360                1365

Tyr Thr Thr Gly Glu Met Phe Asp Val Ser Val Asn Asn Tyr
    1370                1375                1380

Ser Glu Cys Lys Ala Leu Ile Glu Ser Asn Gln Thr Ala Arg Trp
    1385                1390                1395

Lys Asn Val Lys Val Asn Phe Asp Asn Val Gly Leu Gly Tyr Leu
    1400                1405                1410

Ser Leu Leu Gln Val Ala Thr Phe Lys Gly Trp Met Asp Ile Met
    1415                1420                1425

Tyr Ala Ala Val Asp Ser Arg Asn Val Glu Leu Gln Pro Lys Tyr
    1430                1435                1440

Glu Asp Asn Leu Tyr Met Tyr Leu Tyr Phe Val Ile Phe Ile Ile
    1445                1450                1455

Phe Gly Ser Phe Phe Thr Leu Asn Leu Phe Ile Gly Val Ile Ile
    1460                1465                1470

Asp Asn Phe Asn Gln Gln Lys Lys Lys Phe Gly Gly Gln Asp Ile
    1475                1480                1485

Phe Met Thr Glu Glu Gln Lys Lys Tyr Tyr Asn Ala Met Lys Lys
    1490                1495                1500

Leu Gly Ser Lys Lys Pro Gln Lys Pro Ile Pro Arg Pro Ala Asn
    1505                1510                1515

Lys Phe Gln Gly Met Val Phe Asp Phe Val Thr Lys Gln Val Phe
    1520                1525                1530

Asp Ile Ser Ile Met Ile Leu Ile Cys Leu Asn Met Val Thr Met
    1535                1540                1545

Met Val Glu Thr Asp Asp Gln Ser Gln Glu Met Thr Asn Ile Leu
    1550                1555                1560

Tyr Trp Ile Asn Leu Val Phe Ile Val Leu Phe Thr Gly Glu Cys
    1565                1570                1575

Val Leu Lys Leu Ile Ser Leu Arg Tyr Tyr Phe Thr Ile Gly
    1580                1585                1590

Trp Asn Ile Phe Asp Phe Val Val Val Ile Leu Ser Ile Val Gly
    1595                1600                1605

Met Phe Leu Ala Glu Leu Ile Glu Lys Tyr Phe Val Ser Pro Thr
    1610                1615                1620

Leu Phe Arg Val Ile Arg Leu Ala Arg Ile Gly Arg Ile Leu Arg
    1625                1630                1635

Leu Ile Lys Gly Ala Lys Gly Ile Arg Thr Leu Leu Phe Ala Leu
    1640                1645                1650

Met Met Ser Leu Pro Ala Leu Phe Asn Ile Gly Leu Leu Leu Phe
    1655                1660                1665

Leu Val Met Phe Ile Tyr Ala Ile Phe Gly Met Ser Asn Phe Ala
    1670                1675                1680

Tyr Val Lys Arg Glu Val Gly Ile Asp Asp Met Phe Asn Phe Glu
    1685                1690                1695
```

```
Thr Phe Gly Asn Ser Met Ile Cys Leu Phe Gln Ile Thr Thr Ser
    1700            1705                1710

Ala Gly Trp Asp Gly Leu Leu Ala Pro Ile Leu Asn Ser Gly Pro
    1715                1720                1725

Pro Asp Cys Asp Pro Asp Lys Asp His Pro Gly Ser Ser Val Lys
    1730                1735                1740

Gly Asp Cys Gly Asn Pro Ser Val Gly Ile Phe Phe Phe Val Ser
    1745                1750                1755

Tyr Ile Ile Ile Ser Phe Leu Val Val Val Asn Met Tyr Ile Ala
    1760                1765                1770

Val Ile Leu Glu Asn Phe Ser Val Ala Thr Glu Glu Ser Ala Glu
    1775                1780                1785

Pro Leu Ser Glu Asp Asp Phe Glu Met Phe Tyr Glu Val Trp Glu
    1790                1795                1800

Lys Phe Asp Pro Asp Ala Thr Gln Phe Ile Glu Phe Ala Lys Leu
    1805                1810                1815

Ser Asp Phe Ala Asp Ala Leu Asp Pro Pro Leu Leu Ile Ala Lys
    1820                1825                1830

Pro Asn Lys Val Gln Leu Ile Ala Met Asp Leu Pro Met Val Ser
    1835                1840                1845

Gly Asp Arg Ile His Cys Leu Asp Ile Leu Phe Ala Phe Thr Lys
    1850                1855                1860

Arg Val Leu Gly Glu Ser Gly Glu Met Asp Ala Leu Arg Ile Gln
    1865                1870                1875

Met Glu Glu Arg Phe Met Ala Ser Asn Pro Ser Lys Val Ser Tyr
    1880                1885                1890

Glu Pro Ile Thr Thr Thr Leu Lys Arg Lys Gln Glu Glu Val Ser
    1895                1900                1905

Ala Ile Ile Ile Gln Arg Ala Tyr Arg Arg Tyr Leu Leu Lys Gln
    1910                1915                1920

Lys Val Lys Lys Val Ser Ser Ile Tyr Lys Lys Asp Lys Gly Lys
    1925                1930                1935

Glu Cys Asp Gly Thr Pro Ile Lys Glu Asp Thr Leu Ile Asp Lys
    1940                1945                1950

Leu Asn Glu Asn Ser Thr Pro Glu Lys Thr Asp Met Thr Pro Ser
    1955                1960                1965

Thr Thr Ser Pro Pro Ser Tyr Asp Ser Val Thr Lys Pro Glu Lys
    1970                1975                1980

Glu Lys Phe Glu Lys Asp Lys Ser Glu Lys Glu Asp Lys Gly Lys
    1985                1990                1995

Asp Ile Arg Glu Ser Lys Lys
    2000            2005

<210> SEQ ID NO 12
<211> LENGTH: 8876
<212> TYPE: DNA
<213> ORGANISM: Homo sapiens
<220> FEATURE:
<221> NAME/KEY: misc_feature
<223> OTHER INFORMATION: NM_021007.2

<400> SEQUENCE: 12
ggctgcttca gacatatgtc tgtgtgtacg ctgtgaaggt gtttctcttc acagttcccc      60
gccctctagt ggtagttaca ataatgccat tttgtagtcc ctgtacagga aatgcctctt     120
cttacttcag ttaccagaat cctttttacag gaagttaggt gtggtctttg aaggagaatt    180
```

-continued

```
aaaaaaaaaa aaaaaaaaaa aaaaaaaaga tttttttttt tttaaagcat gatggaattt      240
tagctgcagt cttcttggtg ccagcttatc aatcccaaac tctgggtgta aaagattcta      300
cagggcactt tcttatgcaa ggagctaaac agtgattaaa ggagcaggat gaaaagatgg      360
cacagtcagt gctggtaccg ccaggacctg acagcttccg cttctttacc agggaatccc      420
ttgctgctat tgaacaacgc attgcagaag agaaagctaa agacccaaa caggaacgca       480 aggatgagga tgatgaaaat ggcccaaagc caaacagtga cttggaagca ggaaaatctc      540
ttccatttat ttatggagac attcctccag agatggtgtc agtgcccctg gaggatctgg      600
acccctacta tatcaataag aaaacgttta tagtattgaa taagggaaa gcaatctctc       660 gattcagtgc caccctgcc ctttacattt taactcccttc aaccctatt agaaaattag       720 ctattaagat tttggtacat tctttattca atatgctcat tatgtgcacg attcttacca     780
actgtgtatt tatgaccatg agtaaccctc cagactggac aaagaatgtg gagtatacct      840
ttacaggaat ttatactttt gaatcactta ttaaaatact tgcaaggggc ttttgtttag      900
aagatttcac attttttacgg gatccatgga attggttgga tttcacagtc attacttttg    960
catatgtgac agagttttgtg gacctgggca atgtctcagc gttgagaaca ttcagagttc    1020
tccgagcatt gaaaacaatt tcagtcattc caggcctgaa gaccattgtg ggggccctga    1080
tccagtcagt gaagaagctt tctgatgtca tgatcttgac tgtgttctgt ctaagcgtgt    1140
ttgcgctaat aggattgcag ttgttcatgg gcaacctacg aaataaatgt tgcaatggc     1200 ctccagataa ttcttccttt gaaataaata tcacttcctt ctttaacaat tcattggatg    1260
ggaatggtac tactttcaat aggacagtga gcatatttaa ctgggatgaa tatattgagg    1320
ataaaagtca cttttatttt ttagaggggc aaaatgatgc tctgctttgt ggcaacagct    1380
cagatgcagg ccagtgtcct gaaggataca tctgtgtgaa ggctggtaga aaccccaact    1440
atggctacac gagctttgac accttttagtt gggcctttttt gtccttattt cgtctcatga   1500
ctcaagactt ctgggaaaac ctttatcaac tgacactacg tgctgctggg aaaacgtaca    1560
tgatattttt tgtgctggtc attttcttgg gctcattcta tctaataaat ttgatcttgg    1620
ctgtggtggc catggcctat gaggaacaga atcaggccac attggaagag ctgaacaga    1680 aggaagctga atttcagcag atgctcgaac agttgaaaaa gcaacaagaa gaagctcagg    1740
cggcagctgc agccgcatct gctgaatcaa gagacttcag tggtgctggt gggataggag    1800 tttttttcaga gagttcttca gtagcatcta agttgagctc caaaagtgaa aaagagctga   1860
aaaacagaag aaagaaaaag aaacagaaag aacagtctgg agaagaagag aaaaatgaca    1920
gagtccgaaa atcggaatct gaagacagca taagaagaaa aggtttccgt ttttccttgg    1980
aaggaagtag gctgacatat gaaaagagat tttcttctcc acaccagtcc ttactgagca    2040
tccgtggctc ccttttctct ccaagacgca acagtagggc gagccttttc agcttcagag    2100
gtcgagcaaa ggacattggc tctgagaatg actttgctga tgatgagcac agcacctttg    2160
aggacaatga cagccgaaga gactctctgt tcgtgccgca cagacatgga gaacggcgcc    2220
acagcaatgt cagccaggcc agccgtgcct ccaggggtgct ccccatcctg cccatgaatg    2280
ggaagatgca tagcgctgtg gactgcaatg gtgtggtctc cctggtcggg ggcccttcta    2340
ccctcacatc tgctgggcag ctcctaccag agggcacaac tactgaaaca gaaataagaa    2400
agagacggtc cagttcttat catgtttcca tggatttatt ggaagatcct acatcaaggc    2460
aaagagcaat gagtatagcc agtattttga ccaacaccat ggaagaactt gaagaatcca    2520
```

```
gacagaaatg cccaccatgc tggtataaat ttgctaatat gtgtttgatt tgggactgtt    2580
gtaaaccatg gttaaaggtg aaacaccttg tcaacctggt tgtaatggac ccatttgttg    2640
acctggccat caccatctgc attgtcttaa atacactctt catggctatg gagcactatc    2700
ccatgacgga gcagttcagc agtgtactgt ctgttggaaa cctggtcttc acagggatct    2760
tcacagcaga aatgtttctc aagataattg ccatggatcc atattattac tttcaagaag    2820
gctggaatat ttttgatggt tttattgtga gccttagttt aatggaactt ggtttggcaa    2880
atgtggaagg attgtcagtt ctccgatcat tccggctgct ccgagttttc aagttggcaa    2940
aatcttggcc aactctaaat atgctaatta agatcattgg caattctgtg ggggctctag    3000
gaaacctcac cttggtattg gccatcatcg tcttcatttt tgctgtggtc ggcatgcagc    3060
tctttggtaa gagctacaaa gaatgtgtct gcaagatttc caatgattgt gaactcccac    3120
gctggcacat gcatgacttt ttccactcct tcctgatcgt gttccgcgtg ctgtgtggag    3180
agtggataga gaccatgtgg gactgtatgg aggtcgctgg ccaaaccatg tgccttactg    3240
tcttcatgat ggtcatggtg attggaaatc tagtggttca gaacctcttc ttggccttgc    3300
ttttgagttc cttcagttct gacaatcttg ctgccactga tgatgataac gaaatgaata    3360
atctccagat tgctgtggga aggatgcaga aggaatcga ttttgttaaa agaaaaatac    3420
gtgaatttat tcagaaagcc tttgttagga agcagaaagc tttagatgaa attaaaccgc    3480
ttgaagatct aaataataaa aaagacagct gtatttccaa ccataccacc atagaaatag    3540
gcaaagacct caattatctc aaagacggaa atggaactac tagtggcata ggcagcagtg    3600
tagaaaaata tgtcgtggat gaaagtgatt acatgtcatt tataaacaac cctagcctca    3660
ctgtgacagt accaattgct gttggagaat ctgactttga aaatttaaat actgaagaat    3720
tcagcagcga gtcagatatg gaggaaagca agagaagct aaatgcaact agttcatctg    3780
aaggcagcac ggttgatatt ggagctcccg ccgagggaga acagcctgag gttgaacctg    3840
aggaatccct tgaacctgaa gcctgtttta cagaagactg tgtacggaag ttcaagtgtt    3900
gtcagataag catagaagaa ggcaaaggga aactctggtg gaatttgagg aaaacatgct    3960
ataagatagt ggagcacaat tggttcgaaa ccttcattgt cttcatgatt ctgctgagca    4020 gtgggctct ggcctttgaa gatatataca ttgagcagcg aaaaaccatt aagaccatgt    4080
tagaatatgc tgacaaggtt ttcacttaca tattcattct ggaaatgctg ctaaagtggg    4140
ttgcatatgg ttttcaagtg tattttacca atgcctggtg ctggctagac ttcctgattg    4200
ttgatgtctc actggttagc ttaactgcaa atgcctgggg ttactcagaa cttggtgcca    4260
tcaaatccct cagaacacta agagctctga ggccactgag agctttgtcc cggtttgaag    4320
gaatgagggt tgttgtaaat gctctttttag gagccattcc atctatcatg aatgtacttc    4380
tggtttgtct gatcttttgg ctaatattca gtatcatggg agtgaatctc tttgctggca    4440
agttttacca ttgtattaat tacaccactg gagagatgtt tgatgtaagc gtggtcaaca    4500
actacagtga gtgcaaagct ctcattgaga gcaatcaaac tgccaggtgg aaaaatgtga    4560
aagtaaactt tgataacgta ggacttggat atctgtctct acttcaagta gccacgttta    4620
agggatggat ggatattatg tatgcagctg ttgattcacg aaatgtagaa ttacaaccca    4680
agtatgaaga caacctgtac atgtatcttt attttgtcat ctttattatt tttggttcat    4740 tctttaccctt gaatcttttc attggtgtca tcatagataa cttcaaccaa cagaaaaga    4800 agtttggagg tcaagacatt tttatgacag aagaacagaa gaaatactac aatgcaatga    4860
aaaaactggg ttcaaagaaa ccacaaaaac ccatacctcg acctgctaac aaattccaag    4920
```

```
gaatggtctt tgattttgta accaaacaag tctttgatat cagcatcatg atcctcatct    4980
gccttaacat ggtcaccatg atggtggaaa ccgatgacca gagtcaagaa atgacaaaca    5040
ttctgtactg gattaatctg tgtttattg ttctgttcac tggagaatgt gtgctgaaac     5100
tgatctctct tcgttactac tatttcacta ttggatggaa tattttgat tttgtggtgg     5160 tcattctctc cattgtagga atgtttctgg ctgaactgat agaaaagtat tttgtgtccc    5220
ctaccctgtt ccgagtgatc cgtcttgcca ggattggccg aatcctacgt ctgatcaaag    5280
gagcaaaggg gatccgcacg ctgctctttg ctttgatgat gtcccttcct gcgttgttta    5340
acatcggcct ccttctttc ctggtcatgt tcatctacgc catctttggg atgtccaatt     5400
ttgcctatgt taagagggaa gttgggatcg atgacatgtt caactttgag acctttggca    5460
acagcatgat ctgcctgttc caaattacaa cctctgctgg ctgggatgga ttgctagcac    5520
ctattcttaa tagtggacct ccagactgtg accctgacaa agatcaccct ggaagctcag    5580
ttaaaggaga ctgtgggaac ccatctgttg ggattttctt ttttgtcagt tacatcatca    5640
tatccttcct ggttgtggtg aacatgtaca tcgcggtcat cctggagaac ttcagtgttg    5700
ctactgaaga aagtgcagag cctctgagtg aggatgactt tgagatgttc tatgaggttt    5760
gggagaagtt tgatcccgat gcgacccagt ttatagagtt tgccaaactt tctgattttg    5820
cagatgccct ggatcctcct cttctcatag caaaacccaa caaagtccag ctcattgcca    5880
tggatctgcc catggtgagt ggtgaccgga tccactgtct tgacatctta tttgctttta    5940
caaagcgtgt tttgggtgag agtggagaga tggatgccct tcgaatacag atggaagagc    6000
gattcatggc atcaaacccc tccaaagtct cttatgagcc cattacgacc acgttgaaac    6060
gcaaacaaga ggaggtgtct gctattatta tccagagggc ttacagacgc tacctcttga    6120
agcaaaaagt taaaaaggta tcaagtatat acaagaaaga caaaggcaaa gaatgtgatg    6180
gaacacccat caaagaagat actctcattg ataaactgaa tgagaattca actccagaga    6240
aaaccgatat gacgccttcc accacgtctc caccctcgta tgatagtgtg accaaaccag    6300
aaaaagaaaa attttgaaaaa gacaaatcag aaaaggaaga caaagggaaa gatatcaggg    6360
aaagtaaaaa gtaaaagaa accaagaatt ttccattttg tgatcaattg tttacagccc      6420
gtgatggtga tgtgttttgtg tcaacaggac tcccacagga ggtctatgcc aaactgactg    6480
tttttacaaa tgtatactta aggtcagtgc ctataacaag acagagacct ctggtcagca    6540
aactggaact cagtaaactg gagaaatagt atcgatggga ggtttctatt ttcacaacca    6600
gctgacactg ctgaagagca gaggcgtaat ggctactcag acgataggaa ccaatttaaa    6660
ggggggaggg aagttaaatt tttatgtaaa ttcaacatgt gacacttgat aatagtaatt    6720
gtcaccagtg tttatgtttt aactgccaca cctgccatat ttttacaaaa cgtgtgctgt    6780
gaatttatca cttttctttt taattcacag gttgttact attatatgtg actattttg      6840 taaatgggtt tgtgtttggg gagagggatt aaagggaggg aattctacat ttctctattg    6900
tattgtataa ctggatatat tttaaatgga ggcatgctgc aattctcatt cacacataaa    6960
aaaatcacat cacaaagggg aagagtttac ttcttgtttc aggatgtttt tagattttg     7020 aggtgcttaa atagctattc gtattttaa ggtgtctcat ccagaaaaaa tttaatgtgc     7080
ctgtaaatgt tccatagaat cacaagcatt aaagagttgt tttatttta cataacccat     7140 taaatgtaca tgtatatatg tatatatgta tatgtgcgtg tatatacata tatatgtata    7200
cacacatgca cacacagaga tatacacata ccattacatt gtcattcaca gtcccagcag    7260
```

```
catgactatc acatttttga taagtgtcct ttggcataaa ataaaaatat cctatcagtc    7320 cttttctaaga agcctgaatt gaccaaaaaa catccccacc accactttat aaagttgatt    7380
ctgctttatc ctgcagtatt gtttagccat cttctgctct tggtaaggtt gacatagtat    7440
atgtcaattt aaaaaataaa agtctgcttt gtaaatagta attttaccca gtggtgcatg    7500
tttgagcaaa caaaaatgat gatttaagca cactacttat tgcatcaaat atgtaccaca    7560
gtaagtatag tttgcaagct ttcaacaggt aaatatgatgt aattggttcc attatagttt    7620
gaagctgtca ctgctgcatg tttatcttgc ctatgctgct gtatcttatt ccttccactg    7680
ttcagaagtc taatatggga agccatatat cagtggtaaa gtgaagcaaa ttgttctacc    7740
aagacctcat tcttcatgtc attaagcaat aggttgcagc aaacaaggaa gagcttcttg    7800 cttttattc ttccaaccttt aattgaacac tcaatgatga aaagcccgac tgtacaaaca    7860
tgttgcaagc tgcttaaatc tgtttaaaat atatggttag agttttctaa gaaaatataa    7920
atactgtaaa aagttcattt tattttattt ttcagccttt tgtacgtaaa atgagaaatt    7980
aaaagtatct tcaggtggat gtcacagtca ctattgttag tttctgttcc tagcactttt    8040
aaattgaagc acttcacaaa ataagaagca aggactagga tgcagtgtag gtttctgctt    8100
ttttattagt actgtaaact tgcacacatt tcaatgtgaa acaaatctca aactgagttc    8160
aatgtttatt tgctttcaat agtaatgcct tatcattgaa agaggcttaa agaaaaaaaa    8220
aatcagctga tactcttggc attgcttgaa tccaatgttt ccacctagtc tttttattca    8280
gtaatcatca gtcttttcca atgtttgttt acacagatag atcttattga cccatatggc    8340
actagaactg tatcagatat aatatgggat cccagctttt tttcctctcc cacaaaacca    8400
ggtagtgaag ttatattacc agttacagca aaatactttg tgtttcacaa gcaacaataa    8460
atgtagattc tttatactga agctattgac ttgtagtgtg ttggtgaaat gcatgcagga    8520
aaatgctgtt accataaaga acggtaaacc acattacaat caagccaaaa gaataaaggt    8580
ttcgcttttg ttttgtatt taattgttgt ctttgtttct atctttgaaa tgccattta    8640 aggtagattt ctatcatgta aaaataatct atctgaaaaa caaatgtaaa gaacacacat    8700
taattactat aattcatctt tcaatttttt catggaatgg aagttaatta agaagagtgt    8760
attggataac tactttaata ttggccaaaa agctagatat ggcatcaggt agactagtgg    8820
aaagttacaa aaattaataa aaaattgact aacattttaa aaaaaaaaaa aaaaaa       8876
```

ANTISENSE OLIGONUCLEOTIDES TARGETING SCN2A FOR THE TREATMENT OF SCN1A ENCEPHALOPATHIES

CROSS-REFERENCE TO RELATED APPLICATIONS

This application is the national stage of International (PCT) Patent Application Serial Number PCT/US2019/047313, filed Aug. 20, 2019, which claims priority to and the benefit of U.S. Provisional Patent Application No. 62/765,344, filed Aug. 20, 2018, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on 19 Apr. 2022, is named 0411_0036-PCT-US_ST25.txt and is 31,558 bytes in size.

FIELD OF THE INVENTION

Provided herein are methods, compounds, and compositions useful for reducing expression of sodium voltage-gated channel alpha subunit 2 (SCN2A) in a subject (e.g., a human). Also, provided herein are methods, compounds, and compositions comprising SCN2A antisense oligonucleotides (ASOs), which can be useful in treating diseases or conditions related to sodium voltage-gated channel alpha subunit 1 (SCN1A) in a subject. Such methods, compounds, and compositions can be useful, for example, to treat, prevent, delay or ameliorate an SCN1A-related encephalopathy, such as Dravet syndrome.

BACKGROUND OF THE INVENTION

The sodium voltage-gated channel alpha subunit 1 (SCN1A) gene is located on the long (q) arm of human chromosome 2 at position 24.3, that encodes NaV1.1, the alpha subunit of a voltage-gated sodium channel that is expressed in the brain and involved in neural signaling. Mutations in SCN1A may be associated with epilepsy, generalized epilepsy with febrile seizures, familial febrile seizures, migraines, early infantile epileptic encephalopathy 6, Dravet syndrome (severe myoclonic epilepsy of infancy), and other SCN1A related encephalopathies. However, the mechanism by which SCN1A mutations causes adverse effects is not well-understood in the art, and satisfactory methods of treating SCN1A encephalopathies are not available. Thus, there remains a need for new methods useful for treating these SCN1A-related disorders.

SUMMARY OF THE INVENTION

Provided herein are compositions, compounds and methods for modulating expression of sodium voltage-gated channel alpha subunit 2 (SCN2A) in order to treat sodium voltage-gated channel alpha subunit 1 (SCN1A)-associated diseases such as SCN1A encephalopathies, including Dravet syndrome (severe myoclonic epilepsy of infancy (SMEI)), epilepsy, generalized epilepsy with febrile seizures, familial febrile seizures, migraines, and early infantile epileptic encephalopathy 6.

In one aspect, the invention features a method of treating an SCN1A encephalopathy in a subject in need thereof by administering to the subject a compound comprising a single-stranded oligonucleotide that is 10-80 nucleosides in length and having a nucleobase sequence comprising a portion of 10 contiguous nucleobases having at least 80% complementary to an equal length portion of a target region of a pre-mRNA transcript or an mRNA transcript of a human SCN2A gene, in an amount and for a duration sufficient to treat the SCN1A encephalopathy.

In some embodiments, the method decreases expression of the human SCN2A gene.

In some embodiments, the oligonucleotide includes, consists essentially of, or consists of a nucleobase sequence complementary to a portion of SCN2A mRNA that encodes the amino acid sequence of GenBank accession no. NP_066287.2 or includes the nucleobase sequence of GenBank accession no. NM 021007.2.

In some embodiments, the oligonucleotide includes one or more modified sugar, one or more modified internucleoside linkages, and/or one or more modified nucleobases.

In some embodiments, the oligonucleotide includes one or more modified sugars.

In some embodiments, each of the one or more modified sugars is independently selected from the group consisting of a bicyclic sugar, a 2'-O-methoxyethyl (2MOE) modified sugar, a 2'-O-methoxy (2-OMe) modified sugar, a 2'-methoxy modified sugar, a 2'-O-alkyl modified sugar, a constrained ethyl (cEt) modified sugar, a locked sugar, and an unlocked sugar.

In some embodiments, the oligonucleotide has 2MOE modified sugars throughout the length of the oligonucleotide.

In some embodiments, the oligonucleotide includes one or more modified internucleoside linkages.

In some embodiments, one or more of the modified internucleoside linkages includes a modified phosphate.

In some embodiments, each of the modified phosphates is independently selected from the group consisting of a phosphorothioate, a phosphorodithioate, a phosphoramidate, a phosphorodiamidate, a thiophosphoramidate, a thiophosphorodiamidate, a methyl phosphonate, a phosphoromorpholidate, and a phosphoropiperazidate.

In some embodiments, the oligonucleotide has phosphorothioate internucleoside linkages throughout the length of the oligonucleotide.

In some embodiments, the oligonucleotide has phosphorodiamidate morpholino internucleoside linkages throughout the length of the oligonucleotide.

In some embodiments, the oligonucleotide includes one or more modified nucleobases.

In some embodiments, the modified nucleobase is selected from the group consisting of 5-methylcytosine, 5-hydroxymethyl cytosine, xanthine, hypoxanthine, 2-aminoadenine, 6-methyladenine, 6-methylguanine, 2-propyladenine, 2-propylguanine, 2-thiouracil, 2-thiothymine, 2-thiocytosine, 5-halouracil, 5-halocytosine, 5-propynyluracil, 5-propynylcytosine, 6-azouracil, 6-azocytosine, 6-azothymine, 5-uracil (pseudouracil), 4-thiouracil, 8-haloadenine, 8-aminoadenine, 8-thioladenine, 8-thioalkyladenine, 8-hydroxyladenine, 8-haloguanine, 8-aminoguanine, 8-thiolguanine, 8-thioalkylguanine, 8-hydroxylguanine, 5-bromouracil, 5-trifluoromethyluracil, 5-bromocytosine, 5-trifluoromethylcytosine, 7-methylguanine, 7-methyladenine, 2-fluoroadenine, 8-azaguanine, 8-azaadenine, 7-deazaguanine, 7-deazaadenine, 3-deazaguanine, and 3-deazaadenine.

In some embodiments, the modified nucleobase is a 5-methylcytosine.

In some embodiments, each cytosine is a 5-methylcytosine.

In some embodiments, the modified oligonucleotide comprises:
  a gap segment consisting of linked deoxynucleosides;
  a 5' wing segment consisting of linked nucleosides; and
  a 3' wing segment consisting of linked nucleosides;
  wherein the gap segment is positioned immediately adjacent to and between the 5' wing segment and the 3' wing segment and wherein each nucleoside of each wing segment comprises a modified sugar.

In some embodiments, the oligonucleotide consists of 12 to 40 (e.g., 16 to 30) nucleobases.

In some embodiments, the method includes inhibiting the expression of SCN2A in neuronal cells in the subject.

In some embodiments, the SCN1A encephalopathy is selected from the group consisting of epilepsy, generalized epilepsy with febrile seizures, familial febrile seizures, migraines, early infantile epileptic encephalopathy 6, and Dravet syndrome.

In some embodiments, the SCN1A encephalopathy is Dravet syndrome.

In some embodiments, the compound is administered intrathecally, intramedullary, or intracerebroventricularly.

In some embodiments, decreased expression of SCN2A provides a therapeutic effect.

In some embodiments, the method reduces one or more symptoms of the SCN1A encephalopathy.

In some embodiments, the one or more symptoms of the SCN1A encephalopathy is selected form the group consisting of prolonged seizures, frequent seizures, behavioral and developmental delays, movement and balance issues, orthopedic conditions, delayed language and speech issues, growth and nutrition issues, sleeping difficulties, chronic infection, sensory integration disorder, disruption of the autonomic nervous system, and sweating.

In some embodiments, the oligonucleotide is selective for SCN2A pre-mRNA or mRNA over SCN1A pre-mRNA or mRNA.

In some embodiments, the method does not substantially reduce expression of SCN1A.

In some embodiments, the subject has a gain-of-function mutation in SCN1A.

In some embodiments, the subject has a loss-of-function mutation in SCN1A.

Definitions

Unless otherwise indicated, the following terms have the following meanings:

"2'-deoxynucleoside" means a nucleoside comprising 2'-H(H) furanosyl sugar moiety, as found in naturally occurring deoxyribonucleic acids (DNA). In certain embodiments, a 2'-deoxynucleoside may comprise a modified nucleobase or may comprise an RNA nucleobase (uracil).

"2'-O-methoxyethyl" (also 2'-MOE and 2'-O($CH_2$)$_2$—$OCH_3$) refers to an O-methoxy-ethyl modification at the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" or "2-modified nucleoside" means a nucleoside comprising a 2'-substituted or 2'-modified sugar moiety. As used herein, "2'-substituted" or "2-modified" in reference to a sugar moiety means a sugar moiety comprising at least one 2'-substituent group other than H or OH.

"3' target site" refers to the nucleotide of a target nucleic acid which is complementary to the 3'-most nucleotide of a particular compound.

"5' target site" refers to the nucleotide of a target nucleic acid which is complementary to the 5'-most nucleotide of a particular compound.

"5-methylcytosine" means a cytosine with a methyl group attached to the 5 position.

"About" means within ±10% of a value. For example, if it is stated, "the compounds affected about 70% inhibition of a SCN2A", it is implied that SCN2A levels are inhibited within a range of 60% and 80%.

"Administration" or "administering" refers to routes of introducing a compound or composition provided herein to a subject to perform its intended function. An example of a route of administration that can be used includes, but is not limited to intrathecal, intramedullar, intracerebroventricular, and parenteral administration, such as subcutaneous, intravenous, or intramuscular injection or infusion.

"Administered concomitantly" or "co-administration" means administration of two or more compounds in any manner in which the pharmacological effects of both are manifest in the patient. Concomitant administration does not require that both compounds be administered in a single pharmaceutical composition, in the same dosage form, by the same route of administration, or at the same time. The effects of both compounds need not manifest themselves at the same time. The effects need only be overlapping for a period of time and need not be coextensive. Concomitant administration or co-administration encompasses administration in parallel or sequentially.

"Amelioration" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Antisense activity" means any detectable and/or measurable activity attributable to the hybridization of an antisense compound to its target nucleic acid. In certain embodiments, antisense activity is a decrease in the amount or expression of a target nucleic acid or protein encoded by such target nucleic acid compared to target nucleic acid levels or target protein levels in the absence of the antisense compound to the target.

"Antisense compound" means a compound comprising an oligonucleotide and optionally one or more additional features, such as a conjugate group or terminal group. Examples of antisense compounds include single-stranded and double-stranded compounds, such as, oligonucleotides, ribozymes, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels in the absence of the antisense compound.

"Antisense mechanisms" are all those mechanisms involving hybridization of a compound with target nucleic acid, wherein the outcome or effect of the hybridization is either target degradation or target occupancy with concomitant stalling of the cellular machinery involving, for example, transcription or splicing.

"Antisense oligonucleotide" means an oligonucleotide having a nucleobase sequence that is complementary to a target nucleic acid or region or segment thereof. In certain embodiments, an antisense oligonucleotide is specifically hybridizable to a target nucleic acid or region or segment thereof.

"Ataxia" means the loss of full control of bodily movements.

"Bicyclic nucleoside" or "BNA" means a nucleoside comprising a bicyclic sugar moiety. "Bicyclic sugar" or "bicyclic sugar moiety" means a modified sugar moiety comprising two rings, wherein the second ring is formed via a bridge connecting two of the atoms in the first ring thereby forming a bicyclic structure. In certain embodiments, the first ring of the bicyclic sugar moiety is a furanosyl moiety. In certain embodiments, the bicyclic sugar moiety does not comprise a furanosyl moiety.

"Branching group" means a group of atoms having at least 3 positions that are capable of forming covalent linkages to at least 3 groups. In certain embodiments, a branching group provides a plurality of reactive sites for connecting tethered ligands to an oligonucleotide via a conjugate linker and/or a cleavable moiety.

"Chemical modification" in a compound describes the substitutions or changes through chemical reaction, of any of the units in the compound. "Modified nucleoside" means a nucleoside having, independently, a modified sugar moiety and/or modified nucleobase. "Modified oligonucleotide" means an oligonucleotide comprising at least one modified internucleoside linkage, a modified sugar, and/or a modified nucleobase.

"Chemically distinct region" refers to a region of a compound that is in some way chemically different than another region of the same compound. For example, a region having 2'-O-methoxyethyl nucleotides is chemically distinct from a region having nucleotides without 2'-O-methoxyethyl modifications.

"Chimeric antisense compounds" means antisense compounds that have at least 2 chemically distinct regions, each position having a plurality of subunits.

"Cleavable bond" means any chemical bond capable of being split. In certain embodiments, a cleavable bond is selected from among: an amide, a polyamide, an ester, an ether, one or both esters of a phosphodiester, a phosphate ester, a carbamate, a di-sulfide, or a peptide.

"Cleavable moiety" means a bond or group of atoms that is cleaved under physiological conditions, for example, inside a cell, an animal, or a human.

"Complementary" in reference to an oligonucleotide means the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to the following pairs: adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Contiguous" in the context of an oligonucleotide refers to nucleosides, nucleobases, sugar moieties, or internucleoside linkages that are immediately adjacent to each other. For example, "contiguous nucleobases" means nucleobases that are immediately adjacent to each other in a sequence.

"Dementia" means a continued loss of intellectual function that impairs memory, judgment, and thought.

"Designing" or "Designed to" refer to the process of designing a compound that specifically hybridizes with a selected nucleic acid molecule.

"Diluent" means an ingredient in a composition that lacks pharmacological activity, but is pharmaceutically necessary or desirable. For example, the diluent in an injected composition can be a liquid, e.g., saline solution.

"Differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

"Dose" means a specified quantity of a compound or pharmaceutical agent provided in a single administration, or in a specified time period. In certain embodiments, a dose may be administered in two or more boluses, tablets, or injections. For example, in certain embodiments, where subcutaneous administration is desired, the desired dose may require a volume not easily accommodated by a single injection. In such embodiments, two or more injections may be used to achieve the desired dose. In certain embodiments, a dose may be administered in two or more injections to minimize injection site reaction in a subject. In other embodiments, the compound or pharmaceutical agent is administered by infusion over an extended period of time or continuously. Doses may be stated as the amount of pharmaceutical agent per hour, day, week or month.

"Dosing regimen" is a combination of doses designed to achieve one or more desired effects.

"Double-stranded compound" means a compound comprising two oligomeric compounds that are complementary to each other and form a duplex, and wherein one of the two said oligomeric compounds comprises an oligonucleotide.

"Effective amount" means the amount of compound sufficient to effectuate a desired physiological outcome in a subject in need of the compound. The effective amount may vary among subjects depending on the health and physical condition of the subject to be treated, the taxonomic group of the subjects to be treated, the formulation of the composition, assessment of the subject's medical condition, and other relevant factors.

"Efficacy" means the ability to produce a desired effect.

"Ensembl ID" is an identification number consisting of letters and numbers assigned to a gene sequence by Ensembl, which is a joint project between EMBL-EBI and the Wellcome Trust Sanger Institute to develop a software system that produces and maintains automatic annotation of selected eukaryotic genomes. Ensembl annotation helps identify a gene location in a particular genome and can be used to configure the equivalent gene on another species' genome.

"Epilepsy" is a central nervous system disorder in which nerve cell activity in the brain becomes chronically disrupted. In certain instances, it may cause seizures, periods of unusual behavior, sensations, and sometimes loss of consciousness. In certain instances, it may also cause other symptoms including myoclonus, cognitive deficits, learning disabilities, or developmental delay in children. In certain instances, it may lead to death in some patients. In certain instances, some forms of epilepsy are associated with progressive neurodegenerative diseases. Many people with epilepsy have more than one symptom.

"Expression" includes all the functions by which a gene's coded information is converted into structures present and operating in a cell. Such structures include, but are not limited to the products of transcription and translation.

"Gapmer" means an oligonucleotide comprising an internal region having a plurality of nucleosides that support RNase H cleavage positioned between external regions having one or more nucleosides, wherein the nucleosides comprising the internal region are chemically distinct from the nucleoside or nucleosides comprising the external regions. The internal region may be referred to as the "gap" and the external regions may be referred to as the "wings."

"SCN1A" means human sodium voltage-gated channel alpha subunit 1 and refers to any nucleic acid of SCN1A. For example, in certain embodiments, SCN1A includes a DNA sequence encoding SCN1A, an RNA sequence transcribed from DNA encoding SCN1A (including genomic DNA comprising introns and exons). The target may be referred to in either upper or lower case.

"SCN2A" means human sodium voltage-gated channel alpha subunit 2 and refers to any nucleic acid of SCN2A. For example, in certain embodiments, SCN2A includes a DNA sequence encoding SCN2A, an RNA sequence transcribed from DNA encoding SCN2A (including genomic DNA comprising introns and exons). The target may be referred to in either upper or lower case.

"SCN2A-specific inhibitor" refers to any agent capable of specifically inhibiting SCN2A expression or activity at the molecular level. For example, SCN2A-specific inhibitors include nucleic acids (including antisense compounds), peptides, antibodies, small molecules, and other agents capable of inhibiting the expression or activity of SCN2A.

"Hybridization" means annealing of oligonucleotides and/or nucleic acids. While not limited to a particular mechanism, the most common mechanism of hybridization involves hydrogen bonding, which may be Watson-Crick, Hoogsteen or reversed Hoogsteen hydrogen bonding, between complementary nucleobases. In certain embodiments, complementary nucleic acid molecules include, but are not limited to, an antisense compound and a nucleic acid target. In certain embodiments, complementary nucleic acid molecules include, but are not limited to, an oligonucleotide and a nucleic acid target.

"Immediately adjacent" means there are no intervening elements between the immediately adjacent elements of the same kind (e.g., no intervening nucleobases between the immediately adjacent nucleobases).

"Subject" means a human or non-human animal selected for treatment or therapy.

"Inhibiting the expression or activity" refers to a reduction or blockade of the expression or activity relative to the expression of activity in an untreated or control sample and does not necessarily indicate a total elimination of expression or activity.

"Internucleoside linkage" means a group or bond that forms a covalent linkage between adjacent nucleosides in an oligonucleotide. "Modified internucleoside linkage" means any internucleoside linkage other than a naturally occurring, phosphate internucleoside linkage. Non-phosphate linkages are referred to herein as modified internucleoside linkages.

"Intracerebroventricular administration" means administration in the ventricular system of the brain.

"Intraperitoneal administration" means administration through infusion or injection into the peritoneum.

"Intramedullary administration" means administration into the spinal cord, the medulla oblongata, or in the marrow cavity of a bone.

"Intrathecal administration" means administration into the spinal canal or into the subarachnoid space so that it reaches the cerebrospinal fluid (CSF).

"Intravenous administration" means administration into a vein.

"Lengthened oligonucleotides" are those that have one or more additional nucleosides relative to an oligonucleotide disclosed herein, e.g., a parent oligonucleotide.

"Linked nucleosides" means adjacent nucleosides linked together by an internucleoside linkage.

"Mismatch" or "non-complementary" means a nucleobase of a first oligonucleotide that is not complementary to the corresponding nucleobase of a second oligonucleotide or target nucleic acid when the first and second oligonucleotides are aligned. For example, nucleobases including but not limited to a universal nucleobase, inosine, and hypoxanthine, are capable of hybridizing with at least one nucleobase but are still mismatched or non-complementary with respect to nucleobase to which it hybridized. As another example, a nucleobase of a first oligonucleotide that is not capable of hybridizing to the corresponding nucleobase of a second oligonucleotide or target nucleic acid when the first and second oligonucleotides are aligned is a mismatch or non-complementary nucleobase.

"Modulating" refers to changing or adjusting a feature in a cell, tissue, organ or organism. For example, modulating SCN2A can mean to increase or decrease the level of SCN2A in a cell, tissue, organ or organism. A "modulator" effects the change in the cell, tissue, organ or organism. For example, a compound can be a modulator of SCN2A that decreases the amount of SCN2A in a cell, tissue, organ or organism.

"MOE" means methoxyethyl.

"Monomer" refers to a single unit of an oligomer. Monomers include, but are not limited to, nucleosides and nucleotides.

"Motif" means the pattern of unmodified and/or modified sugar moieties, nucleobases, and/or internucleoside linkages, in an oligonucleotide.

"Myoclonus" means episodes of repeated, stereotypic, involuntary muscle jerking or twitching that can affect part of the body or the entire body for variable durations.

"Natural" or "naturally occurring" means found in nature.

"Non-bicyclic modified sugar" or "non-bicyclic modified sugar moiety" means a modified sugar moiety that comprises a modification, such as a substituent, that does not form a bridge between two atoms of the sugar to form a second ring.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase, and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric compound" means a compound comprising a single oligonucleotide and optionally one or more additional features, such as a conjugate group or terminal group.

"Oligonucleotide" means a polymer of linked nucleosides each of which can be modified or unmodified, independent one from another. Unless otherwise indicated, oligonucleotides consist of 8-80 linked nucleosides. "Modified oligonucleotide" means an oligonucleotide, wherein at least one sugar, nucleobase, or internucleoside linkage is modified. "Unmodified oligonucleotide" means an oligonucleotide that does not comprise any sugar, nucleobase, or internucleoside modification.

"Parent oligonucleotide" means an oligonucleotide whose sequence is used as the basis of design for more oligonucleotides of similar sequence but with different lengths, motifs, and/or chemistries. The newly designed oligonucleotides may have the same or overlapping sequence as the parent oligonucleotide.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Pharmaceutically acceptable carrier or diluent" means any substance suitable for use in administering to a subject (e.g., a human). For example, a pharmaceutically acceptable carrier can be a sterile aqueous solution, such as PBS or water-for-injection.

"Pharmaceutically acceptable salts" means physiologically and pharmaceutically acceptable salts of compounds, such as oligomeric compounds or oligonucleotides, i.e., salts that retain the desired biological activity of the parent compound and do not impart undesired toxicological effects thereto.

"Pharmaceutical agent" means a compound that provides a therapeutic benefit when administered to a subject.

"Pharmaceutical composition" means a mixture of substances suitable for administering to a subject. For example, a pharmaceutical composition may comprise one or more compounds or salt thereof and a sterile aqueous solution.

"Phosphorothioate linkage" means a modified phosphate linkage in which one of the non-bridging oxygen atoms is replaced with a sulfur atom. A phosphorothioate internucleoside linkage is a modified internucleoside linkage.

"Phosphorus moiety" means a group of atoms comprising a phosphorus atom. In certain embodiments, a phosphorus moiety comprises a mono-, di-, or tri-phosphate, or phosphorothioate.

"Portion" means a defined number of contiguous (i.e., linked) nucleobases of a nucleic acid. In certain embodiments, a portion is a defined number of contiguous nucleobases of a target nucleic acid.

In certain embodiments, a portion is a defined number of contiguous nucleobases of an oligomeric compound.

"Prevent" refers to delaying or forestalling the onset, development or progression of a disease, disorder, or condition for a period of time from minutes to indefinitely.

"Prodrug" means a compound in a form outside the body which, when administered to a subject, is metabolized to another form within the body or cells thereof. In certain embodiments, the metabolized form is the active, or more active, form of the compound (e.g., drug). Typically conversion of a prodrug within the body is facilitated by the action of an enzyme(s) (e.g., endogenous or viral enzyme) or chemical(s) present in cells or tissues, and/or by physiologic conditions.

"Reduce" means to bring down to a smaller extent, size, amount, or number.

"RefSeq No." is a unique combination of letters and numbers assigned to a sequence to indicate the sequence is for a particular target transcript (e.g., target gene). Such sequence and information about the target gene (collectively, the gene record) can be found in a genetic sequence database. Genetic sequence databases include the NCBI Reference Sequence database, GenBank, the European Nucleotide Archive, and the DNA Data Bank of Japan (the latter three forming the International Nucleotide Sequence Database Collaboration or INSDC).

"Region" is defined as a portion of the target nucleic acid having at least one identifiable structure, function, or characteristic.

"RNAi compound" means an antisense compound that acts, at least in part, through RISC or Ago2, but not through RNase H, to modulate a target nucleic acid and/or protein encoded by a target nucleic acid. RNAi compounds include, but are not limited to double-stranded siRNA, single-stranded RNA (ssRNA), and microRNA, including microRNA mimics.

"Segments" are defined as smaller or sub-portions of regions within a nucleic acid.

"Seizures" are a symptom of many different disorders and conditions that can affect the brain. "Seizures" are typically caused by disruptions in the electric communication between neurons in the brain, resulting from a brain injury or a disease or disorder. Seizures can take on different forms and affect different people in different ways. Common physical changes that may occur during a seizure are difficulty talking, inability to swallow, drooling, repeated blinking of the eyes, staring, lack of movement of muscle tone, slumping tremors, twitching, or jerking movements, rigid or tense muscles, repeated non-purposeful movements, called automatisms, involving the face, arms, or legs, convulsions, loss of control of urine or stool, sweating, change in skin color (paleness or flushing), dilation of pupils, biting of tongue, difficulty breathing, heart palpitations. In some embodiments, seizures are mild. In other embodiments, seizures are completely disabling or may result in death. Abnormal brain activity can often be documented by abnormal findings on an electroencephalogram (EEG).

"Side effects" means physiological disease and/or conditions attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded" in reference to a compound means the compound has only one oligonucleotide. "Self-complementary" means an oligonucleotide that at least partially hybridizes to itself. A compound consisting of one oligonucleotide, wherein the oligonucleotide of the compound is self-complementary, is a single-stranded compound. A single-stranded compound may be capable of binding to a complementary compound to form a duplex.

"Sites," are defined as unique nucleobase positions within a target nucleic acid.

"Specifically hybridizable" refers to an oligonucleotide having a sufficient degree of complementarity between the oligonucleotide and a target nucleic acid to induce a desired effect, while exhibiting minimal or no effects on non-target nucleic acids. In certain embodiments, specific hybridization occurs under physiological conditions.

"Specifically inhibit" a target nucleic acid means to reduce or block expression of the target nucleic acid while exhibiting fewer, minimal, or no effects on non-target nucleic acids reduction and does not necessarily indicate a total elimination of the target nucleic acid's expression.

"Standard cell assay" means assay(s) described in the Examples and reasonable variations thereof.

"Standard in vivo experiment" means the procedure(s) described in the Example(s) and reasonable variations thereof.

"Subject" refers to a human or non-human animal, including, but not limited to, mice, rats, rabbits, dogs, cats, pigs, and non-human primates, including, but not limited to, monkeys and chimpanzees.

"Sugar moiety" means an unmodified sugar moiety or a modified sugar moiety. "Unmodified sugar moiety" or "unmodified sugar" means a 2'-OH(H) furanosyl moiety, as found in RNA (an "unmodified RNA sugar moiety"), or a 2'-H(H) moiety, as found in DNA (an "unmodified DNA sugar moiety"). Unmodified sugar moieties have one hydrogen at each of the 1', 3', and 4' positions, an oxygen at the 3' position, and two hydrogens at the 5' position. "Modified sugar moiety" or "modified sugar" means a modified furanosyl sugar moiety or a sugar surrogate. "Modified furanosyl sugar moiety" means a furanosyl sugar comprising a non-hydrogen substituent in place of at least one hydrogen of an unmodified sugar moiety. In certain embodiments, a modified furanosyl sugar moiety is a 2'-substituted sugar moiety. Such modified furanosyl sugar moieties include bicyclic sugars and non-bicyclic sugars.

"Sugar surrogate" means a modified sugar moiety having other than a furanosyl moiety that can link a nucleobase to another group, such as an internucleoside linkage, conjugate group, or terminal group in an oligonucleotide. Modified nucleosides comprising sugar surrogates can be incorporated into one or more positions within an oligonucleotide and such oligonucleotides are capable of hybridizing to complementary oligomeric compounds or nucleic acids.

"Subcutaneous administration" means administration just below the skin.

"Target gene" refers to a gene encoding a target.

"Targeting" means specific hybridization of a compound that to a target nucleic acid in order to induce a desired effect.

"Target nucleic acid," "target RNA," "target RNA transcript" and "nucleic acid target" all mean a nucleic acid capable of being targeted by compounds described herein.

"Target region" means a portion of a target nucleic acid to which one or more compounds is targeted.

"Target segment" means the sequence of nucleotides of a target nucleic acid to which a compound described herein is targeted. "5' target site" refers to the 5'-most nucleotide of a target segment. "3' target site" refers to the 3'-most nucleotide of a target segment.

"Terminal group" means a chemical group or group of atoms that is covalently linked to a terminus of an oligonucleotide.

"Therapeutically effective amount" means an amount of a compound, pharmaceutical agent, or composition that provides a therapeutic benefit to a subject.

"Treat" refers to administering a compound or pharmaceutical composition to a subject in order to effect an alteration or improvement of a disease, disorder, or condition in the subject.

DETAILED DESCRIPTION

Figure 1A:
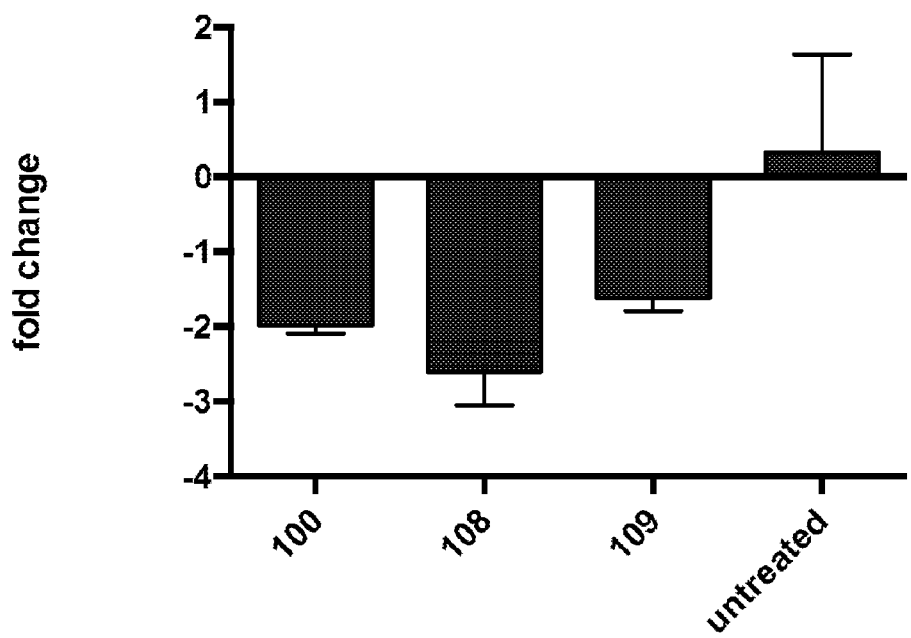
FIGS. 1A-1B are graphs showing changes in SCN2A mRNA level in mice heterozygous for the SCN2A R1882Q mutation at P15 (n=3 for all treatment groups) (FIG. 1A) and P35 (ASO 1 n=4, ASO 2 n=4, ASO 3 n=1, untreated n=3) (FIG. 1B). The fold change was normalized to age matched, untreated wildtype. All mice were injected at P1-P2.

It is to be understood that both the foregoing general description and the following detailed description are exemplary and explanatory only and are not restrictive of the embodiments, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting.

The section headings used herein are for organizational purposes only and are not to be construed as limiting the subject matter described. All documents, or portions of documents, cited in this application, including, but not limited to, patents, patent applications, articles, books, treatises, and GenBank and NCBI reference sequence records are hereby expressly incorporated by reference for the portions of the document discussed herein, as well as in their entirety.

It is understood that the sequence set forth in each SEQ ID NO in the examples contained herein is independent of any modification to a sugar moiety, an internucleoside linkage, or a nucleobase. As such, compounds defined by a SEQ ID NO may comprise, independently, one or more modifications to a sugar moiety, an internucleoside linkage, or a nucleobase. Compounds described by ISIS number (ISIS #) indicate a combination of nucleobase sequence, chemical modification, and motif.

The present invention is based in part upon the discovery that oligonucleotides that target the SCN2A gene are useful for treating subjects with an SCN1A encephalopathy. Accordingly, the invention features methods for preventing and treating SCN1A encephalopathies in a subject by administering oligonucleotides that target the SCN2A gene.

Certain Embodiments

Certain embodiments provide methods, compounds, and compositions for modulating an SCN1A encephalopathy (e.g., Dravet syndrome) or a symptom thereof, in a subject by administering the compound or composition to the subject, wherein the compound or composition comprises a SCN2A modulator. Modulation of SCN2A can lead to a decrease of SCN2A level or expression in order to reduce SCN2A expression in order to treat, prevent, ameliorate or delay an SCN1A encephalopathy, or a symptom thereof. In certain embodiments, the SCN2A modulator is a SCN2A-specific inhibitor. In certain embodiments, SCN2A-specific inhibitors are nucleic acids (including antisense compounds), peptides, antibodies, small molecules, and other agents capable of inhibiting the expression or activity of SCN2A. In certain embodiments, the subject is a human.

In some certain embodiments, the oligonucleotide is selective for SCN2A pre-mRNA or mRNA over SCN1A pre-mRNA or mRNA. In certain embodiments, the method does not substantially reduce expression of SCN1A. In certain embodiments the subject has a gain-of-function mutation in SCN1A. In certain embodiments, the subject has a loss-of-function mutation in SCN1A.

Certain embodiments disclosed herein provide compounds or compositions comprising a SCN2A modulator. Such compounds or compositions are useful to treat, prevent, ameliorate, or delay the onset of a SCN1A encephalopathy (e.g., Dravet syndrome), or a symptom thereof. In certain embodiments, the compound comprises a SCN2A-specific inhibitor. In certain embodiments, the SCN2A-specific inhibitor is a nucleic acid, polypeptide, antibody, small molecules, or other agent capable of inhibiting the expression or activity of SCN2A. In certain embodiments, a SCN2A-specific inhibitor is a nucleic acid targeting SCN2A. In certain embodiments, the nucleic acid is single stranded. In certain embodiments, the nucleic acid is double stranded. In certain embodiments, the compound or composition comprises an antisense compound. In any of the foregoing embodiments, the compound or composition comprises an oligomeric compound. In certain embodiments, the compound or composition comprises an oligonucleotide targeting SCN2A. In certain embodiments, the oligonucleotide is single stranded. In certain embodiments, the compound comprises deoxyribonucleotides. In certain embodiments, the compound comprises ribonucleotides and is double-stranded. In certain embodiments, the oligonucleotide is a modified oligonucleotide. In certain embodiments, the modified oligonucleotide is single stranded.

In any of the foregoing embodiments, the compound can comprise a modified oligonucleotide 8 to 80, 10 to 30, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked nucleosides in length.

In certain embodiments, at least one internucleoside linkage of said modified oligonucleotide is a modified internucleoside linkage. In certain embodiments, at least one internucleoside linkage is a phosphorothioate internucleoside linkage. In certain embodiments, the internucleoside linkages are phosphorothioate linkages and phosphate ester linkages.

In certain embodiments, any of the foregoing oligonucleotides comprises at least one modified sugar. In certain embodiments, at least one modified sugar comprises a 2'-O-methoxyethyl group. In certain embodiments, at least one modified sugar is a bicyclic sugar, such as a 4'-CH(CH$_3$)—O-2' group, a 4'-CH$_2$—O-2' group, or a 4'-(CH$_2$)$_2$—O-2' group.

In certain embodiments, at least one nucleoside of said modified oligonucleotide comprises a modified nucleobase. In certain embodiments, the modified nucleobase is a 5-methylcytosine.

In certain embodiments, a compound or composition comprises a modified oligonucleotide comprising: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar. In certain embodiments, at least one internucleoside linkage is a phosphorothioate linkage. In certain embodiments, and at least one cytosine is a 5-methylcytosine.

In certain embodiments, a compound comprises a modified oligonucleotide 12 to 80 linked nucleosides in length. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length.

In certain embodiments, the compounds or compositions disclosed herein further comprise a pharmaceutically acceptable carrier or diluent.

In certain embodiments, the compound or composition is co-administered with a second agent. In certain embodiments, the compound and the second agent are administered concomitantly.

In certain embodiments, compounds and compositions described herein targeting SCN2A can be used in methods of inhibiting expression of SCN2A in a cell. In certain embodiments, compounds and compositions described herein targeting SCN2A can be used in methods of treating, preventing, delaying, or ameliorating a SCN1A related disease or disorder, including, but not limited to, Dravet syndrome Certain Indications Certain embodiments provided herein relate to methods of inhibiting SCN2A expression or activity, which can be useful for treating, preventing, or ameliorating a disease associated with SCN1A in a subject, by administration of a compound or composition that targets SCN2A. In certain embodiments, such a compound or composition comprises a SCN2A-specific inhibitor. In certain embodiments, the compound comprises an antisense compound or an oligomeric compound targeted to SCN2A. In certain embodiments, the compound comprises a modified oligonucleotide targeted to SCN2A.

In certain embodiments, a method of inhibiting expression or activity of SCN2A in a cell comprises contacting the cell with a compound or composition comprising a SCN2A-specific inhibitor, thereby inhibiting the expression or activity of SCN2A in the cell. In certain embodiments, the cell is a neuron. In certain embodiments, the cell is in the brain tissue. In certain embodiments, the cell is in the brain tissue of a subject who has, or is at risk of having a disease, disorder, condition, symptom, or physiological marker associated with an SCN1A disorder. In certain embodiments, the SCN1A disease or disorder is Dravet syndrome. In certain embodiments, the SCN1A disease is epilepsy. In certain embodiments, the SCN1A disease is generalized epilepsy with febrile seizures. In certain embodiments, the SCN1A disease is familial febrile seizures. In certain embodiments, the SCN1A disease is early infantile epileptic encephalopathy 6. In certain embodiments, the SCN2A-specific inhibitor is a nucleic acid, peptide, antibody, small molecule or other agent capable of inhibiting the expression or activity of the SCN2A. In certain embodiments, the SCN2A-specific inhibitor is an antisense compound or an oligomeric compound targeted to SCN2A. In certain embodiments, the SCN2A-specific inhibitor is oligonucleotide targeted to SCN2A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, a method of treating, preventing, delaying the onset, slowing the progression, or ameliorating one or more disease, disorders, conditions, symptoms, or physiological markers associated with SCN1A comprises administering to the subject a compound or composition comprising a SCN2A-specific inhibitor. In certain embodiments, a method of treating, preventing, delaying the onset, slowing the progression, or ameliorating a disease, disorder, condition, symptom, or physiological marker associated with a with a SCN1A related disease or disorder in a subject comprises administering to the subject a compound or composition comprising a SCN2A-specific inhibitor, thereby treating, preventing, delaying the onset, slowing the progression, or ameliorating the disease. In certain embodiments, the subject is identified as having, or at risk of having, the disease, disorder, condition, symptom or physiological marker. In certain embodiments, the SCN1A disease or disorder is Dravet syndrome. In certain embodiments, the SCN1A disease is epilepsy. In certain embodiments, the SCN1A disease is generalized epilepsy with febrile seizures. In certain embodiments, the SCN1A disease is familial febrile seizures. In certain embodiments, the SCN1A disease is early infantile epileptic encephalopathy 6. In certain embodiments, the SCN2A-specific inhibitor is administered to the subject parenterally. In certain embodiments, the parenteral administration is intracerebroventricular administration. In certain embodiments, the parenteral administration is intrathecal administration. In certain embodiments, the parenteral administration is subcutaneous administration. In certain embodiments, the subject is a human. In certain embodiments, the SCN2A-specific inhibitor is a nucleic acid, peptide, antibody, small molecule or other agent capable of inhibiting the expression or activity of SCN2A. In certain embodiments, the SCN2A-specific inhibitor comprises an antisense compound or an oligomeric compound targeted to SCN2A. In certain embodiments, the SCN2A-specific inhibitor is an oligonucleotide targeted to SCN2A. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, a method of reducing seizures, decreasing myoclonus or muscle spasms, alleviating difficulty in walking (peripheral neuropathy), spasticity, reducing, preventing the onset of, or treating dementia, alleviating difficulties in speech, reducing or preventing the onset of visual hallucinations, treating, reducing or preventing the onset of progressive neurologic degeneration, treating, reducing, or preventing the onset of damage to nerves that control bladder function, lessening hypotonia, improving muscle tone, reducing or preventing the onset of an enlarged liver, reducing or preventing the onset of heart defects, reducing or preventing the accumulation of polyglucosan bodies in a cell, improving or preventing cognitive deterioration, and reducing ataxia, or a combination thereof, in a subject comprises administering to the subject a compound or composition comprising a SCN2A-specific inhibitor. In certain embodiments, the cell is a neuron. In certain embodiments, administering the compound or composition reduces seizures in the subject. In certain embodiments, administering the compound or composition decreases myoclonus or muscle spasms in the subject. In certain embodiments, administering the compound or composition alleviates difficulty in walking in the subject. In certain embodiments, administering the compound or composition alleviates peripheral neuropathy in the subject. In certain embodiments, administering the compound or composition alleviates spasticity in the subject. In certain embodiments, administering the compound or composition reduces, prevents the onset of, or treats dementia in the subject. In certain embodiments, administering the compound or composition alleviates difficulties in speech in the subject. In certain embodiments, administering the compound or composition reduces or prevents the onset of visual hallucinations in the subject. In certain embodiments, administering the compound or composition treats, reduces or prevents the onset of progressive neurologic degeneration in the subject. In certain embodiments, administering the compound or composition treats, reduces or prevents the onset of damage to the nerves that control bladder function in the subject. In certain embodiments, administering the compound or composition treats, reduces or prevents the onset of hypotonia in the subject. In certain embodiments, administering the compound or composition improves muscle tone in the subject. In certain embodiments, administering the compound or composition improves or prevents cognitive deterioration. In certain embodiments, administering the compound or composition treats or reduces ataxia in the subject. In certain embodiments, administering the compound or composition treats, reduces, or prevents one or more of prolonged seizures, frequent seizures, behavioral and developmental delays, movement and balance issues, orthopedic conditions, delayed language and speech issues, growth and nutrition issues, sleeping difficulties, chronic infection, sensory integration disorder, disruption of the autonomic nervous system, and sweating. In certain embodiments, the subject is identified as having, or at risk of having a disease, disorder, condition, symptom, or physiological marker associated with SCN1A. In certain embodiments, the SCN1A disease or disorder is Dravet syndrome. In certain embodiments, the SCN1A disease is epilepsy. In certain embodiments, the SCN1A disease is generalized epilepsy with febrile seizures. In certain embodiments, the SCN1A disease is familial febrile seizures. In certain embodiments, the SCN1A disease is early infantile epileptic encephalopathy 6. In certain embodiments, the SCN2A-specific inhibitor is administered to the subject parenterally. In certain embodiments, the parenteral administration is intracerebroventricular administration. In certain embodiments, the parenteral administration is intrathecal administration. In certain embodiments, the administration is intramedullar administration. In certain embodiments, the parenteral administration is subcutaneous administration. In certain embodiments, the subject is a human. In certain embodiments, the SCN2A-specific inhibitor is a nucleic acid, peptide, antibody, small molecule or other agent capable of inhibiting the expression or activity of the SCN2A. In certain embodiments, the SCN2A-specific inhibitor is an antisense compound or an oligomeric compound targeted to SCN2A. In certain embodiments, the SCN2A-specific inhibitor is oligonucleotide targeted to SCN2A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

In certain embodiments, administering the compound or composition disclosed herein decreases seizures, decreases myoclonus or muscle spasms, alleviates difficulty in walking, alleviates spasticity, reduces, prevents the onset of or treats dementia, alleviates difficulties in speech, reduces or prevents the onset of visual hallucinations, treats, reduces or prevents the onset of progressive neurologic degeneration, treating, reducing, or preventing the onset of damage to nerves that control bladder function, lessening hypotonia, improving muscle tone, improves cognitive deterioration, and reduces ataxia, or a combination thereof. In certain embodiments, seizures were independently reduced by at least 5%, at least 10%, at least 20%, at least 30%, at least 35%, at least 40%, at least 45% or at least 50%. In certain embodiments, myoclonus or muscle spasms were independently reduced by at least 5%, at least 10%, at least 20%, at least 30%, at least 35%, at least 40%, at least 45% or at least 50%. In certain embodiments, difficulty in walking was independently alleviated by at least 5%, at least 10%, at least 20%, at least 30%, at least 35%, at least 40%, at least 45% or at least 50%. In certain embodiments, spasticity was independently reduced by at least 5%, at least 10%, at least 20%, at least 30%, at least 35%, at least 40%, at least 45% or at least 50%. In certain embodiments, difficulty in speech was independently alleviated by at least 5%, at least 10%, at least 20%, at least 30%, at least 35%, at least 40%, at least 45% or at least 50%. In certain embodiments, visual hallucinations were independently reduced by at least 5%, at least 10%, at least 20%, at least 30%, at least 35%, at least 40%, at least 45% or at least 50%. In certain embodiments, progressive neurologic degeneration was independently reduced by at least 5%, at least 10%, at least 20%, at least 30%, at least 35%, at least 40%, at least 45% or at least 50%. In certain embodiments, dementia progression was independently reduced by at least 5%, at least 10%, at least 20%, at least 30%, at least 35%, at least 40%, at least 45% or at least 50%. In certain embodiments, nerve damage of bladder function independently reduced by at least 5%, at least 10%, at least 20%, at least 30%, at least 35%, at least 40%, at least 45% or at least 50%. In certain embodiments, hypotonia was independently reduced by at least 5%, at least 10%, at least 20%, at least 30%, at least 35%, at least 40%, at least 45% or at least 50%. In certain embodiments, cognitive deterioration was reduced by at least 5%, at least 10%, at least 20%, at least 30%, at least 35%, at least 40%, at least 45% or at least 50%. In certain embodiments, ataxia was independently reduced by at least 5%, at least 10%, at least 20%, at least 30%, at least 35%, at least 40%, at least 45% or at least 50%. In certain embodiments, the cell is a neuron.

Certain embodiments provide compounds and compositions described herein for use in therapy. Certain embodiments are drawn to a compound or composition comprising a SCN2A-specific inhibitor for use in treating, preventing, delaying the onset, slowing the progression, or ameliorating one or more diseases, disorders, conditions, symptoms, or physiological markers associated with SCN1A. Certain embodiments are drawn to a compound or composition for use in treating, preventing, delaying the onset, slowing the progression, or ameliorating an SCN1A disease or disorder, or a symptom or physiological marker thereof. In certain embodiments, the SCN1A disease or disorder is Dravet syndrome. In certain embodiments, the SCN1A disease is epilepsy. In certain embodiments, the SCN1A disease is generalized epilepsy with febrile seizures. In certain embodiments, the SCN1A disease is familial febrile seizures. In certain embodiments, the SCN1A disease is early infantile epileptic encephalopathy 6.

In certain embodiments, the SCN1A disease or disorder is Dravet syndrome. In certain embodiments, the SCN2A-specific inhibitor is a nucleic acid, peptide, antibody, small molecule or other agent capable of inhibiting the expression or activity of the SCN2A. In certain embodiments, the SCN2A-specific inhibitor is an antisense compound or an oligomeric compound targeted to SCN2A. In certain embodiments, the SCN2A-specific inhibitor is oligonucleotide targeted to SCN2A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

Certain embodiments are drawn to a compound or composition comprising a SCN2A-specific inhibitor for use in reducing seizures, decreasing myoclonus or muscle spasms, alleviating difficulty in walking, reducing, preventing the onset of, or treating dementia, alleviating difficulties in speech, reducing or preventing the onset of visual hallucinations, treating, reducing or preventing the onset of progressive neurologic degeneration, treating, reducing, or preventing the onset of damage to nerves that control bladder function, lessening hypotonia, improving muscle tone, improving or preventing cognitive deterioration, and reducing ataxia, or a combination thereof, in a subject. In certain embodiments, administering the compound or composition reduces seizures in the subject. In certain embodiments, administering the compound or composition decreases myoclonus or muscle spasms in the subject. In certain embodiments, administering the compound or composition alleviates difficulty in walking in the subject. In certain embodiments, administering the compound or composition reduces, prevents the onset of, or treats dementia in the subject. In certain embodiments, administering the compound or composition alleviates difficulties in speech in the subject. In certain embodiments, administering the compound or composition reduces or prevents the onset of visual hallucinations in the subject. In certain embodiments, administering the compound or composition treats, reduces or prevents the onset of progressive neurologic degeneration in the subject. In certain embodiments, administering the compound or composition treats, reduces, or prevents the onset of damage to nerves that control bladder function in the subject. In certain embodiments, administering the compound or composition treats, reduces, or prevents hypotonia in the subject. In certain embodiments, administering the compound or composition improves muscle tone in the subject. In certain embodiments, the cell is a neuron. In certain embodiments, administering the compound or composition improves or prevents cognitive deterioration. In certain embodiments, administering the compound or composition treats, reduces ataxia in the subject. In certain embodiments, the subject is identified as having, or at risk of having a disease, disorder, condition, symptom, or physiological marker associated with an SCN1A disease or disorder. In certain embodiments, the SCN1A disease or disorder is Dravet syndrome. In certain embodiments, the SCN1A disease is epilepsy. In certain embodiments, the SCN1A disease is generalized epilepsy with febrile seizures. In certain embodiments, the SCN1A disease is familial febrile seizures. In certain embodiments, the SCN1A disease is early infantile epileptic encephalopathy 6. In certain embodiments, the subject is a human. In certain embodiments, the SCN2A-specific inhibitor is a nucleic acid, peptide, antibody, small molecule or other agent capable of inhibiting the expression or activity of the SCN2A. In certain embodiments, the SCN2A-specific inhibitor is an antisense compound or an oligomeric compound targeted to SCN2A. In certain embodiments, the SCN2A-specific inhibitor is oligonucleotide targeted to SCN2A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound comprising a modified oligonucleotide can be single-stranded. In certain embodiments, the compound comprising a modified oligonucleotide can be double-stranded.

Certain embodiments are drawn to the use of compounds or compositions described herein for the manufacture or preparation of a medicament for therapy. Certain embodiments are drawn to the use of a compound or composition as described herein in the manufacture or preparation of a medicament for treating, preventing, delaying the onset, slowing progression, or ameliorating one or more diseases, disorders, conditions, symptoms, or physiological markers associated with SCN1A. In certain embodiments, the compound or composition as described herein is used in the manufacture or preparation of a medicament for treating, ameliorating, delaying or preventing an SCN1A disease or disorder. In certain embodiments, the SCN1A disease or disorder is Dravet syndrome. In certain embodiments, the SCN1A disease is epilepsy. In certain embodiments, the SCN1A disease is generalized epilepsy with febrile seizures. In certain embodiments, the SCN1A disease is familial febrile seizures. In certain embodiments, the SCN1A disease is early infantile epileptic encephalopathy 6. In certain embodiments, the compound or composition comprises a nucleic acid, peptide, antibody, small molecule or other agent capable of inhibiting the expression or activity of SCN2A. In certain embodiments, the compound or composition comprises an antisense compound or an oligomeric compound targeted to SCN2A. In certain embodiments, the compound or composition comprises an oligonucleotide targeted to SCN2A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

Certain embodiments are drawn to the use of a compound or composition for the manufacture or preparation of a medicament for reducing seizures, decreasing myoclonus or muscle spasms, alleviating difficulty in walking, reducing, preventing the onset of, or treating dementia, alleviating difficulties in speech, reducing or preventing the onset of visual hallucinations, treating, reducing or preventing the onset of progressive neurologic degeneration, treating, reducing, or preventing the onset of damage to nerves that control bladder function, lessening hypotonia, improving muscle tone, improving or preventing cognitive deterioration, and reducing ataxia, or a combination thereof, in a subject having or at risk of having an SCN1A disease or disorder. In certain embodiments, the cell is a neuron. Certain embodiments are drawn to use of a compound or composition in the manufacture or preparation of a medicament for reducing seizures in the subject. Certain embodiments are drawn to use of a compound or composition in the manufacture or preparation of a medicament for decreasing myoclonus or muscle spasms in the subject. Certain embodiments are drawn to use of a compound or composition in the manufacture or preparation of a medicament for alleviating difficulty in walking in the subject. Certain embodiments are drawn to use of a compound or composition in the manufacture or preparation of a medicament for reducing, preventing the onset of, or treating dementia in the subject. Certain embodiments are drawn to use of a compound or composition in the manufacture or preparation of a medicament alleviating difficulties in speech in the subject. Certain embodiments are drawn to use of a compound or composition in the manufacture or preparation of a medicament reducing or preventing the onset of visual hallucinations in the subject. Certain embodiments are drawn to use of a compound or composition in the manufacture or preparation of a medicament treating, reducing or preventing the onset of progressive neurologic degeneration in the subject. Certain embodiments are drawn to the use of a compound or composition in the manufacture or preparation of a medicament for treating, reducing, or preventing the onset of damage to nerves that control bladder function in the subject. Certain embodiments are drawn to the use of a compound or composition in the manufacture or preparation of a medicament for treating, reducing, or preventing hypotonia in the subject. Certain embodiments are drawn to the use of a compound or composition in the manufacture or preparation of a medicament for improving muscle tone in the subject. Certain embodiments are drawn to use of a compound or composition in the manufacture or preparation of a medicament reducing ataxia in the subject. In certain embodiments, the cell is a neuron. In certain embodiments, the compound or composition comprises a nucleic acid, peptide, antibody, small molecule or other agent capable of inhibiting the expression or activity of the SCN2A. In certain embodiments, the compound or composition comprises an antisense compound or an oligomeric compound targeted to SCN2A. In certain embodiments, the compound or composition comprises an oligonucleotide targeted to SCN2A. In certain embodiments, the compound or composition comprises a modified oligonucleotide 8 to 80 linked nucleosides in length. In certain embodiments, the compound or composition comprises a modified oligonucleotide 10 to 30 linked nucleosides in length. In certain embodiments, the compound or composition comprising a modified oligonucleotide can be single-stranded. In certain embodiments, the compound or composition comprising a modified oligonucleotide can be double-stranded.

In any of the foregoing methods or uses, the compound or composition can comprise an antisense compound targeted to SCN2A. In certain embodiments, the compound comprises an oligonucleotide, for example an oligonucleotide consisting of 8 to 80 linked nucleosides, 10 to 30 linked nucleosides, 12 to 30 linked nucleosides, or 20 linked nucleosides. In certain embodiments, the oligonucleotide comprises at least one modified internucleoside linkage, at least one modified sugar and/or at least one modified nucleobase. In certain embodiments, the modified internucleoside linkage is a phosphorothioate internucleoside linkage, the modified sugar is a bicyclic sugar or a 2'-O-methoxyethyl, and the modified nucleobase is a 5-methylcytosine. In certain embodiments, the modified oligonucleotide comprises a gap segment consisting of linked deoxynucleosides; a 5' wing segment consisting of linked nucleosides; and a 3' wing segment consisting of linked nucleosides, wherein the gap segment is positioned immediately adjacent to and between the 5' wing segment and the 3' wing segment and wherein each nucleoside of each wing segment comprises a modified sugar. In certain embodiments, the compound can comprise a modified oligonucleotide 12 to 80 linked nucleosides in length. In certain embodiments, the compound is an antisense compound or oligomeric compound. In certain embodiments, the compound is single-stranded. In certain embodiments, the compound is double-stranded. In certain embodiments, the modified oligonucleotide is 12 to 30 linked nucleosides in length. In certain embodiments, the compounds or compositions disclosed herein further comprise a pharmaceutically acceptable carrier or diluent.

In any of the foregoing methods or uses, the compound or composition comprises or consists of a modified oligonucleotide 12 to 30 linked nucleosides in length, wherein the modified oligonucleotide comprises:
a gap segment consisting of linked 2'-deoxynucleosides;
a 5' wing segment consisting of linked nucleosides; and
a 3' wing segment consisting of linked nucleosides;
  wherein the gap segment is positioned between the 5' wing segment and the 3' wing segment and wherein each nucleoside of each wing segment comprises a modified sugar.

In any of the foregoing methods or uses, the compound or composition can be administered parenterally. For example, in certain embodiments the compound or composition can be administered through injection or infusion. Parenteral administration includes subcutaneous administration, intravenous administration, intramuscular administration, intraarterial administration, intraperitoneal administration, or intracranial administration. In certain embodiments, the compound or composition is co-administered with a second agent. In certain embodiments, the compound or composition and the second agent are administered concomitantly. In any of the foregoing methods or uses, the compound or composition can be administered intrathecally. In any of the foregoing methods or uses, the compound or composition can be administered intramedullary. In any of the foregoing methods or uses, the compound or composition can be administered intracerebroventricularly.

Certain Compounds

In certain embodiments, compounds described herein are antisense compounds. In certain embodiments, the antisense compound comprises or consists of an oligomeric compound. In certain embodiments, the oligomeric compound comprises a modified oligonucleotide. In certain embodiments, the modified oligonucleotide has a nucleobase sequence complementary to that of a target nucleic acid.

In certain embodiments, a compound described herein comprises or consists of a modified oligonucleotide. In certain embodiments, the modified oligonucleotide has a nucleobase sequence complementary to that of a target nucleic acid.

In certain embodiments, a compound or antisense compound is single-stranded. Such a single-stranded compound or antisense compound comprises or consists of an oligomeric compound. In certain embodiments, such an oligomeric compound comprises or consists of an oligonucleotide. In certain embodiments, the oligonucleotide is an antisense oligonucleotide. In certain embodiments, the oligonucleotide is modified. In certain embodiments, the oligonucleotide of a single-stranded antisense compound or oligomeric compound comprises a self-complementary nucleobase sequence.

In certain embodiments, compounds are double-stranded. Such double-stranded compounds comprise a first modified oligonucleotide having a region complementary to a target nucleic acid and a second modified oligonucleotide having a region complementary to the first modified oligonucleotide. In certain embodiments, the modified oligonucleotide is an RNA oligonucleotide. In such embodiments, the thymine nucleobase in the modified oligonucleotide is replaced by a uracil nucleobase. In certain embodiments, compound comprises a conjugate group. In certain embodiments, each modified oligonucleotide is 12-30 linked nucleosides in length.

In certain embodiments, compounds are double-stranded. Such double-stranded compounds comprise a first oligomeric compound having a region complementary to a target nucleic acid and a second oligomeric compound having a region complementary to the first oligomeric compound. The first oligomeric compound of such double stranded compounds typically comprises or consists of a modified oligonucleotide. The oligonucleotide of the second oligomeric compound of such double-stranded compound may be modified or unmodified. The oligomeric compounds of double-stranded compounds may include non-complementary overhanging nucleosides.

Examples of single-stranded and double-stranded compounds include but are not limited to oligonucleotides, siRNAs, microRNA targeting oligonucleotides, and single-stranded RNAi compounds, such as small hairpin RNAs (shRNAs), single-stranded siRNAs (ssRNAs), and microRNA mimics.

In certain embodiments, a compound described herein has a nucleobase sequence that, when written in the 5' to 3' direction, comprises the reverse complement of the target segment of a target nucleic acid to which it is targeted.

In certain embodiments, a compound described herein comprises an oligonucleotide 10 to 30 linked subunits in length. In certain embodiments, compound described herein comprises an oligonucleotide is 12 to 30 linked subunits in length. In certain embodiments, compound described herein comprises an oligonucleotide is 12 to 22 linked subunits in length. In certain embodiments, compound described herein comprises an oligonucleotide is 14 to 30 linked subunits in length. In certain embodiments, compound described herein comprises an oligonucleotide is 14 to 20 linked subunits in length. In certain embodiments, compound described herein comprises an oligonucleotide is 15 to 30 linked subunits in length. In certain embodiments, compound described herein comprises an oligonucleotide is 15 to 20 linked subunits in length. In certain embodiments, compound described herein comprises an oligonucleotide is 16 to 30 linked subunits in length. In certain embodiments, compound described herein comprises an oligonucleotide is 16 to 20 linked subunits in length. In certain embodiments, compound described herein comprises an oligonucleotide is 17 to 30 linked subunits in length. In certain embodiments, compound described herein comprises an oligonucleotide is 17 to 20 linked subunits in length. In certain embodiments, compound described herein comprises an oligonucleotide is 18 to 30 linked subunits in length. In certain embodiments, compound described herein comprises an oligonucleotide is 18 to 21 linked subunits in length. In certain embodiments, compound described herein comprises an oligonucleotide is 18 to 20 linked subunits in length. In certain embodiments, compound described herein comprises an oligonucleotide is 20 to 30 linked subunits in length. In other words, such oligonucleotides are from 12 to 30 linked subunits, 14 to 30 linked subunits, 14 to 20 subunits, 15 to 30 subunits, 15 to 20 subunits, 16 to 30 subunits, 16 to 20 subunits, 17 to 30 subunits, 17 to 20 subunits, 18 to 30 subunits, 18 to 20 subunits, 18 to 21 subunits, 20 to 30 subunits, or 12 to 22 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 22, 18 to 24, 18 to 30, 18 to 50, 19 to 22, 19 to 30, 19 to 50, or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the linked subunits are nucleotides, nucleosides, or nucleobases.

In certain embodiments, compounds may be shortened or truncated. For example, a single subunit may be deleted from the 5' end (5' truncation), or alternatively from the 3' end (3' truncation). A shortened or truncated compound targeted to a SCN2A nucleic acid may have two subunits deleted from the 5' end, or alternatively may have two subunits deleted from the 3' end, of the compound. Alternatively, the deleted nucleosides may be dispersed throughout the compound.

When a single additional subunit is present in a lengthened compound, the additional subunit may be located at the 5' or 3' end of the compound. When two or more additional subunits are present, the added subunits may be adjacent to each other, for example, in a compound having two subunits added to the 5' end (5' addition), or alternatively to the 3' end (3' addition), of the compound. Alternatively, the added subunits may be dispersed throughout the compound.

It is possible to increase or decrease the length of a compound, such as an oligonucleotide, and/or introduce mismatch bases without eliminating activity (Woolf et al. (Proc. Natl. Acad. Sci. USA 89:7305-7309, 1992; Gautschi et al. *J. Natl. Cancer Inst.* 93:463-471, March 2001; Maher and Dolnick *Nuc. Acid. Res.* 16:3341-3358, 1988). However, seemingly small changes in oligonucleotide sequence, chemistry and motif can make large differences in one or more of the many properties required for clinical development (Seth et al. *J. Med. Chem.*, 52, 10, 2009; Egli et al. *J. Am. Chem. Soc.*, 133, 16642, 2011).

In certain embodiments, compounds described herein are interfering RNA compounds (RNAi), which include double-stranded RNA compounds (also referred to as short-interfering RNA or siRNA) and single-stranded RNAi compounds (or ssRNA). Such compounds work at least in part through the RISC pathway to degrade and/or sequester a target nucleic acid (thus, include microRNA/microRNA-mimic compounds). As used herein, the term siRNA is meant to be equivalent to other terms used to describe nucleic acid molecules that are capable of mediating sequence specific RNAi, for example short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically modified siRNA, post-transcriptional gene silencing RNA (ptgsRNA), and others. In addition, as used herein, the term RNAi is meant to be equivalent to other terms used to describe sequence specific RNA interference, such as post transcriptional gene silencing, translational inhibition, or epigenetics.

In certain embodiments, a double-stranded compound comprises a first strand comprising the nucleobase sequence complementary to a target region of a SCN2A nucleic acid and a second strand. In certain embodiments, the double-stranded compound comprises ribonucleotides in which the first strand has uracil (U) in place of thymine (T) and is complementary to a target region. In certain embodiments, a double-stranded compound comprises (i) a first strand comprising a nucleobase sequence complementary to a target region of a SCN2A nucleic acid, and (ii) a second strand. In certain embodiments, the double-stranded compound comprises one or more modified nucleotides in which the 2' position in the sugar contains a halogen (such as fluorine group; 2'-F) or contains an alkoxy group (such as a methoxy group; 2'-OMe). In certain embodiments, the double-stranded compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the dsRNA compound. In certain embodiments, the double-stranded compound comprises one or more linkages between adjacent nucleotides other than a naturally-occurring phosphodiester linkage. Examples of such linkages include phosphoramide, phosphorothioate, and phosphorodithioate linkages. The double-stranded compounds may also be chemically modified nucleic acid molecules as taught in U.S. Pat. No. 6,673,661. In other embodiments, the dsRNA contains one or two capped strands, as disclosed, for example, by WO 00/63364, filed Apr. 19, 2000. In certain embodiments, the first strand of the double-stranded compound is an siRNA guide strand and the second strand of the double-stranded compound is an siRNA passenger strand. In certain embodiments, the second strand of the double-stranded compound is complementary to the first strand. In certain embodiments, each strand of the double-stranded compound consists of 16, 17, 18, 19, 20, 21, 22, or 23 linked nucleosides.

In certain embodiments, a single-stranded compound described herein can comprise any of the oligonucleotide sequences targeted to SCN2A described herein. In certain embodiments, such a single-stranded compound is a single-stranded RNAi (ssRNAi) compound. In certain embodiments, a ssRNAi compound comprises the nucleobase sequence complementary to a target region of a SCN2A nucleic acid. In certain embodiments, the ssRNAi compound comprises ribonucleotides in which uracil (U) is in place of thymine (T). In certain embodiments, ssRNAi compound comprises a nucleobase sequence complementary to a target region of a SCN2A nucleic acid. In certain embodiments, a ssRNAi compound comprises one or more modified nucleotides in which the 2' position in the sugar contains a halogen (such as fluorine group; 2'-F) or contains an alkoxy group (such as a methoxy group; 2'-OMe). In certain embodiments, a ssRNAi compound comprises at least one 2'-F sugar modification and at least one 2'-OMe sugar modification. In certain embodiments, the at least one 2'-F sugar modification and at least one 2'-OMe sugar modification are arranged in an alternating pattern for at least 2, 3, 4, 5, 6, 7, 8, 9, 10, 11, 12, 13, 14, 15, 16, 17, 18, 19, or 20 contiguous nucleobases along a strand of the ssRNAi compound. In certain embodiments, the ssRNAi compound comprises one or more linkages between adjacent nucleotides other than a naturally-occurring phosphodiester linkage. Examples of such linkages include phosphoramide, phosphorothioate, and phosphorodithioate linkages. The ssRNAi compounds may also be chemically modified nucleic acid molecules as taught in U.S. Pat. No. 6,673,661. In other embodiments, the ssRNAi contains a capped strand, as disclosed, for example, by WO 00/63364, filed Apr. 19, 2000. In certain embodiments, the ssRNAi compound consists of 16, 17, 18, 19, 20, 21, 22, or 23 linked nucleosides.

In certain embodiments, compounds described herein comprise modified oligonucleotides. Certain modified oligonucleotides have one or more asymmetric center and thus give rise to enantiomers, diastereomers, and other stereoisomeric configurations that may be defined, in terms of absolute stereochemistry, as (R) or (S), as α or β, such as for sugar anomers, or as (D) or (L) such as for amino acids etc. Included in the modified oligonucleotides provided herein are all such possible isomers, including their racemic and optically pure forms, unless specified otherwise. Likewise, all cis- and trans-isomers and tautomeric forms are also included.

Certain Mechanisms

In certain embodiments, compounds described herein comprise or consist of modified oligonucleotides. In certain embodiments, compounds described herein are antisense compounds. In certain embodiments, such antisense compounds comprise oligomeric compounds. In certain embodiments, compounds described herein are capable of hybridizing to a target nucleic acid, resulting in at least one antisense activity. In certain embodiments, compounds described herein selectively affect one or more target nucleic acid. Such selective compounds comprise a nucleobase sequence that hybridizes to one or more target nucleic acid, resulting in one or more desired antisense activity and does not hybridize to one or more non-target nucleic acid or does not hybridize to one or more non-target nucleic acid in such a way that results in a significant undesired antisense activity.

In certain antisense activities, hybridization of a compound described herein to a target nucleic acid results in recruitment of a protein that cleaves the target nucleic acid. For example, certain compounds described herein result in RNase H mediated cleavage of the target nucleic acid. RNase H is a cellular endonuclease that cleaves the RNA strand of an RNA:DNA duplex. The DNA in such an RNA:DNA duplex need not be unmodified DNA. In certain embodiments, compounds described herein are sufficiently "DNA-like" to elicit RNase H activity. Further, in certain embodiments, one or more non-DNA-like nucleoside in the gap of a gapmer is tolerated.

In certain antisense activities, compounds described herein or a portion of the compound is loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to a target nucleic acid results in alteration of translation of the target nucleic acid.

Antisense activities may be observed directly or indirectly. In certain embodiments, observation or detection of an antisense activity involves observation or detection of a change in an amount of a target nucleic acid or protein encoded by such target nucleic acid, a change in the ratio of splice variants of a nucleic acid or protein, and/or a phenotypic change in a cell or animal.

Target Nucleic Acids, Target Regions and Nucleotide Sequences

In certain embodiments, compounds described herein comprise or consist of an oligonucleotide comprising a region that is complementary to a target nucleic acid. In certain embodiments, the target nucleic acid is an endogenous RNA molecule. In certain such embodiments, the target nucleic acid is selected from: an mRNA and a pre-mRNA, including intronic, exonic and untranslated regions. In certain embodiments, the target nucleic acid is a pre-mRNA. In certain such embodiments, the target region is entirely within an intron. In certain embodiments, the target region spans an intron/exon junction. In certain embodiments, the target region is at least 50% within an intron.

Human gene sequences that encode SCN2A are described in the art (HGNC: 10588; Entrez Gene: 6326; Ensembl: ENSG00000136531; OMIM: 182390; UniProtKB: O99250). The mRNA transcript of SCN2A, thus, can be referred to as SCN2A mRNA or NAV1.2 mRNA including pre-mRNA. SCN2A mRNA includes, for instance, a sequence encoding GenBank NP_066287.2 (e.g., GenBank NM_021007.2, GI: 93141209), as well as other mRNA splice/transcript variants (e.g., GenBank accession: NM_001040143.1, GI: 93141213; NM_001040142.1, GI: 93141211; or other known variants). The mRNA transcript of SCN2A, thus, can be referred to as SCN2A mRNA or NAV2.1 mRNA including pre-mRNA.

Human gene sequences that encode SCN1A are described in the art (HGNC: 10585; Entrez Gene 6323; Ensembl: ENSG00000144285; OMIM: 182389; UniProtKB: P35498). The mRNA transcript of SCN1A, thus, can be referred to as SCN1A mRNA or NAV1.1 mRNA including pre-mRNA.

Hybridization

In some embodiments, hybridization occurs between a compound disclosed herein and a SCN2A nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Hybridization conditions are sequence-dependent and are determined by the nature and composition of the nucleic acid molecules to be hybridized.

Methods of determining whether a sequence is specifically hybridizable to a target nucleic acid are well known in the art. In certain embodiments, the compounds provided herein are specifically hybridizable with a SCN2A nucleic acid.

Complementarity

An oligonucleotide is said to be complementary to another nucleic acid when the nucleobase sequence of such oligonucleotide or one or more regions thereof matches the nucleobase sequence of another oligonucleotide or nucleic acid or one or more regions thereof when the two nucleobase sequences are aligned in opposing directions. Nucleobase matches or complementary nucleobases, as described herein, are limited to adenine (A) and thymine (T), adenine (A) and uracil (U), cytosine (C) and guanine (G), and 5-methyl cytosine (mC) and guanine (G) unless otherwise specified. Complementary oligonucleotides and/or nucleic acids need not have nucleobase complementarity at each nucleoside and may include one or more nucleobase mismatches. An oligonucleotide is fully complementary or 100% complementary when such oligonucleotides have nucleobase matches at each nucleoside without any nucleobase mismatches.

In certain embodiments, compounds described herein comprise or consist of modified oligonucleotides. In certain embodiments, compounds described herein are antisense compounds. In certain embodiments, compounds comprise oligomeric compounds. Non-complementary nucleobases between a compound and a SCN2A nucleic acid may be tolerated provided that the compound remains able to specifically hybridize to a target nucleic acid. Moreover, a compound may hybridize over one or more segments of a SCN2A nucleic acid such that intervening or adjacent segments are not involved in the hybridization event (e.g., a loop structure, mismatch, or hairpin structure).

In certain embodiments, the compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a SCN2A nucleic acid, a target region, target segment, or specified portion thereof. Percent complementarity of a compound with a target nucleic acid can be determined using routine methods.

For example, a compound in which 18 of 20 nucleobases of the compound are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, a compound which is 18 nucleobases in length having four non-complementary nucleobases which are flanked by two regions of complete complementarity with the target nucleic acid would have 77.8% overall complementarity with the target nucleic acid and would thus fall within the scope of the present invention. Percent complementarity of a compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, compounds described herein, or specified portions thereof, are fully complementary (i.e., 100% complementary) to a target nucleic acid, or specified portion thereof. For example, a compound may be fully complementary to a SCN2A nucleic acid, or a target region, or a target segment or target sequence thereof. As used herein, "fully complementary" means each nucleobase of a compound is capable of precise base pairing with the corresponding nucleobases of a target nucleic acid. For example, a 20 nucleobase compound is fully complementary to a target sequence that is 400 nucleobases long, so long as there is a corresponding 20 nucleobase portion of the target nucleic acid that is fully complementary to the compound. Fully complementary can also be used in reference to a specified portion of the first and/or the second nucleic acid. For example, a 20 nucleobase portion of a 30 nucleobase compound can be "fully complementary" to a target sequence that is 400 nucleobases long. The 20 nucleobase portion of the 30 nucleobase compound is fully complementary to the target sequence if the target sequence has a corresponding 20 nucleobase portion wherein each nucleobase is complementary to the 20 nucleobase portion of the compound. At the same time, the entire 30 nucleobase compound may or may not be fully complementary to the target sequence, depending on whether the remaining 10 nucleobases of the compound are also complementary to the target sequence.

In certain embodiments, compounds described herein comprise one or more mismatched nucleobases relative to the target nucleic acid. In certain such embodiments, antisense activity against the target is reduced by such mismatch, but activity against a non-target is reduced by a greater amount. Thus, in certain such embodiments selectivity of the compound is improved. In certain embodiments, the mismatch is specifically positioned within an oligonucleotide having a gapmer motif. In certain such embodiments, the mismatch is at position 1, 2, 3, 4, 5, 6, 7, or 8 from the 5'-end of the gap region. In certain such embodiments, the mismatch is at position 9, 8, 7, 6, 5, 4, 3, 2, 1 from the 3'-end of the gap region. In certain such embodiments, the mismatch is at position 1, 2, 3, or 4 from the 5'-end of the wing region. In certain such embodiments, the mismatch is at position 4, 3, 2, or 1 from the 3'-end of the wing region. In certain embodiments, the mismatch is specifically positioned within an oligonucleotide not having a gapmer motif. In certain such embodiments, the mismatch is at position 1, 2, 3, 4, 5, 6, 7, 8, 9, 10, 11, or 12 from the 5'-end of the oligonucleotide. In certain such embodiments, the mismatch is at position, 2, 3, 4, 5, 6, 7, 8, 9, 10, 11, or 12 from the 3'-end of the oligonucleotide.

The location of a non-complementary nucleobase may be at the 5' end or 3' end of the compound. Alternatively, the non-complementary nucleobase or nucleobases may be at an internal position of the compound. When two or more non-complementary nucleobases are present, they may be contiguous (i.e., linked) or non-contiguous. In one embodiment, a non-complementary nucleobase is located in the wing segment of a gapmer oligonucleotide.

In certain embodiments, compounds described herein that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a SCN2A nucleic acid, or specified portion thereof.

In certain embodiments, compounds described herein that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a SCN2A nucleic acid, or specified portion thereof.

In certain embodiments, compounds described herein also include those which are complementary to a portion of a target nucleic acid. As used herein, "portion" refers to a defined number of contiguous (i.e., linked) nucleobases within a region or segment of a target nucleic acid. A "portion" can also refer to a defined number of contiguous nucleobases of a compound. In certain embodiments, the compounds are complementary to at least an 8 nucleobase portion of a target segment. In certain embodiments, the compounds are complementary to at least a 9 nucleobase portion of a target segment. In certain embodiments, the compounds are complementary to at least a 10 nucleobase portion of a target segment. In certain embodiments, the compounds are complementary to at least an 11 nucleobase portion of a target segment. In certain embodiments, the compounds are complementary to at least a 12 nucleobase portion of a target segment. In certain embodiments, the compounds are complementary to at least a 13 nucleobase portion of a target segment. In certain embodiments, the compounds are complementary to at least a 14 nucleobase portion of a target segment. In certain embodiments, the compounds are complementary to at least a 15 nucleobase portion of a target segment. In certain embodiments, the compounds are complementary to at least a 16 nucleobase portion of a target segment. Also contemplated are compounds that are complementary to at least a 9, 10, 11, 12, 13, 14, 15, 16, 17, 18, 19, 20, or more nucleobase portion of a target segment, or a range defined by any two of these values.

Identity

The compounds provided herein may also have a defined percent identity to a particular nucleotide sequence, SEQ ID NO, or compound represented by a specific Isis number, or portion thereof. In certain embodiments, compounds described herein are antisense compounds or oligomeric compounds. In certain embodiments, compounds described herein are modified oligonucleotides. As used herein, a compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of a compound is calculated according to the number of bases that have identical base pairing relative to the sequence to which it is being compared.

In certain embodiments, compounds described herein, or portions thereof, are, or are at least, 70%, 75%, 80%, 85%, 90%, 91%, 92%, 93%, 94%, 95%, 96%, 97%, 98%, 99% or 100% identical to one or more of the compounds or SEQ ID NOs, or a portion thereof, disclosed herein. In certain embodiments, compounds described herein are about 70%, 75%, 80%, 85%, 90%, 91%, 92%, 93%, 94%, 95%, 96%, 97%, 98%, or 99% identical, or any percentage between such values, to a particular nucleotide sequence, SEQ ID NO, or compound represented by a specific Isis number, or portion thereof, in which the compounds comprise an oligonucleotide having one or more mismatched nucleobases. In certain such embodiments, the mismatch is at position 1, 2, 3, 4, 5, 6, 7, 8, 9, 10, 11, or 12 from the 5'-end of the oligonucleotide. In certain such embodiments, the mismatch is at position 2, 3, 4, 5, 6, 7, 8, 9, 10, 11, or 12 from the 3'-end of the oligonucleotide.

In certain embodiments, compounds described herein are antisense compounds. In certain embodiments, a portion of the compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, compounds described herein are oligonucleotides. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Certain Modified Compounds

In certain embodiments, compounds described herein comprise or consist of oligonucleotides consisting of linked nucleosides. Oligonucleotides may be unmodified oligonucleotides (RNA or DNA) or may be modified oligonucleotides. Modified oligonucleotides comprise at least one modification relative to unmodified RNA or DNA (i.e., comprise at least one modified nucleoside (comprising a modified sugar moiety and/or a modified nucleobase) and/or at least one modified internucleoside linkage).

A. Modified Nucleosides

Modified nucleosides comprise a modified sugar moiety or a modified nucleobase or both a modified sugar moiety and a modified nucleobase.

1. Modified Sugar Moieties

In certain embodiments, sugar moieties are non-bicyclic modified sugar moieties. In certain embodiments, modified sugar moieties are bicyclic or tricyclic sugar moieties. In certain embodiments, modified sugar moieties are sugar surrogates. Such sugar surrogates may comprise one or more substitutions corresponding to those of other types of modified sugar moieties.

In certain embodiments, modified sugar moieties are non-bicyclic modified sugar moieties comprising a furanosyl ring with one or more acyclic substituent, including but not limited to substituents at the 2', 4', and/or 5' positions. In certain embodiments one or more acyclic substituent of non-bicyclic modified sugar moieties is branched. Examples of 2'-substituent groups suitable for non-bicyclic modified sugar moieties include but are not limited to: 2'-F, 2-OCH$_3$ ("OMe" or "O-methyl"), and 2'-O(CH$_2$)$_2$OCH$_3$ ("MOE"). In certain embodiments, 2'-substituent groups are selected from among: halo, allyl, amino, azido, SH, CN, OCN, CF$_3$, OCF$_3$, O—C$_1$-C$_{10}$ alkoxy, O—C$_1$-C$_{10}$ substituted alkoxy, O—C$_1$-C$_{10}$ alkyl, O—C$_1$-C$_{10}$ substituted alkyl, S-alkyl, N(R$_m$)-alkyl, O-alkenyl, S-alkenyl, N(R$_m$)-alkenyl, O-alkynyl, S-alkynyl, N(R$_m$)-alkynyl, O-alkylenyl-O-alkyl, alkynyl, alkaryl, aralkyl, O-alkaryl, O-aralkyl, O(CH$_2$)$_2$SCH$_3$, O(CH$_2$)$_2$ON(R$_m$)(R$_n$) or OCH$_2$C(=O)—N(R$_m$)(R$_n$), where each R$_m$ and R$_n$ is, independently, H, an amino protecting group, or substituted or unsubstituted C$_1$-C$_{10}$ alkyl, and the 2'-substituent groups described in Cook et al., U.S. Pat. No. 6,531,584; Cook et al., U.S. Pat. No. 5,859,221; and Cook et al., U.S. Pat. No. 6,005,087. Certain embodiments of these 2'-substituent groups can be further substituted with one or more substituent groups independently selected from among: hydroxyl, amino, alkoxy, carboxy, benzyl, phenyl, nitro (NO$_2$), thiol, thioalkoxy, thioalkyl, halogen, alkyl, aryl, alkenyl and alkynyl. Examples of 4'-substituent groups suitable for linearly non-bicyclic modified sugar moieties include but are not limited to alkoxy (e.g., methoxy), alkyl, and those described in Manoharan et al., WO 2015/106128. Examples of 5'-substituent groups suitable for non-bicyclic modified sugar moieties include but are not limited to: 5'-methyl (R or S), 5'-vinyl, and 5'-methoxy. In certain embodiments, non-bicyclic modified sugars comprise more than one non-bridging sugar substituent, for example, 2'-F-5'-methyl sugar moieties and the modified sugar moieties and modified nucleosides described in Migawa et al., WO 2008/101157 and Rajeev et al., US2013/0203836.

In certain embodiments, a 2'-substituted nucleoside or 2'-non-bicyclic modified nucleoside comprises a sugar moiety comprising a linear 2'-substituent group selected from: F, NH$_2$, N$_3$, OCF$_3$, OCH$_3$, O(CH$_2$)$_3$NH$_2$, CH$_2$CH=CH$_2$, OCH$_2$CH=CH$_2$, OCH$_2$CH$_2$OCH$_3$, O(CH$_2$)$_2$SCH$_3$, O(CH$_2$)$_2$ON(R$_m$)(R$_n$), O(CH$_2$)$_2$O(CH$_2$)$_2$N(CH$_3$)$_2$, and N-substituted acetamide (OCH$_2$C(=O)—N(R$_m$)(R$_n$)), where each R$_m$ and R$_n$ is, independently, H, an amino protecting group, or substituted or unsubstituted C$_1$-C$_{10}$ alkyl.

In certain embodiments, a 2'-substituted nucleoside or 2'-non-bicyclic modified nucleoside comprises a sugar moiety comprising a linear 2'-substituent group selected from: F, OCF$_3$, OCH$_3$, OCH$_2$CH$_2$OCH$_3$, O(CH$_2$)$_2$SCH$_3$, O(CH$_2$)$_2$ON(CH$_3$)$_2$, O(CH$_2$)$_2$O(CH$_2$)$_2$N(CH$_3$)$_2$, and OCH$_2$C(=O)—N(H)CH$_3$ ("NMA").

In certain embodiments, a 2'-substituted nucleoside or 2'-non-bicyclic modified nucleoside comprises a sugar moiety comprising a linear 2'-substituent group selected from: F, OCH$_3$, and OCH$_2$CH$_2$OCH$_3$.

Nucleosides comprising modified sugar moieties, such as non-bicyclic modified sugar moieties, are referred to by the position(s) of the substitution(s) on the sugar moiety of the nucleoside. For example, nucleosides comprising 2'-substituted or 2-modified sugar moieties are referred to as 2'-substituted nucleosides or 2-modified nucleosides.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' bridging sugar substituents include but are not limited to: 4'-CH$_2$-2', 4'-(CH$_2$)$_{2-2'}$, 4'-CH$_2$—O-2' ("LNA"), S-2', 4'-(CH$_2$)$_2$—O-2' ("ENA"), 4'-CH(CH$_3$)—O-2' (referred to as "constrained ethyl" or "cEt" when in the S configuration), 4'-CH$_2$—O—CH$_2$-2', 4'-CH$_2$—N(R)-2', 4'-CH(CH$_2$OCH$_3$)—O-2' ("constrained MOE" or "cMOE") and analogs thereof (see, e.g., Seth et al., U.S. Pat. No. 7,399,845, Bhat et al., U.S. Pat. No. 7,569,686, Swayze et al., U.S. Pat. No. 7,741,457, and Swayze et al., U.S. Pat. No. 8,022,193), 4'-C(CH$_3$)(CH$_3$)—O-2' and analogs thereof (see, e.g., Seth et al., U.S. Pat. No. 8,278,283), 4'-CH$_2$—N(OCH$_3$)-2' and analogs thereof (see, e.g., Prakash et al., U.S. Pat. No. 8,278,425), 4'-CH$_2$—O—N(CH$_3$)-2' (see, e.g., Allerson et al., U.S. Pat. No. 7,696,345 and Allerson et al., U.S. Pat. No. 8,124,745), 4'-CH$_2$—C(H)(CH$_3$)-2' (see, e.g., Zhou, et al., *J. Org. Chem.*, 2009, 74, 118-134), 4'-CH$_2$—C—(=CH$_2$)-2' and analogs thereof (see e.g., Seth et al., U.S. Pat. No. 8,278,426), 4'-C(R$_a$R$_b$)—N(R)—O-2', 4'-C(R$_a$R$_b$)—O—N(R)-2', 4'-CH$_2$—O—N(R)-2', and 4'-CH$_2$—N(R)—O-2', wherein each R, R$_a$, and R$_b$ is, independently, H, a protecting group, or C$_1$-C$_{12}$ alkyl (see, e.g., Imanishi et al., U.S. Pat. No. 7,427,672).

In certain embodiments, such 4' to 2' bridges independently comprise from 1 to 4 linked groups independently selected from: —[C(R$_a$)(R$_b$)]$_n$—, —[C(R$_a$)(R$_b$)]$_n$—O—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Additional bicyclic sugar moieties are known in the art, see, for example: Freier et al., *Nucleic Acids Research*, 1997, 25(22), 4429-4443, Albaek et al., *J. Org. Chem.*, 2006, 71, 7731-7740, Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 20017, 129, 8362-8379; Elayadi et al., *Curr. Opinion Invens. Drugs*, 2001, 2, 558-561; Braasch et al., *Chem. Biol.*, 2001, 8, 1-7; Orum et al., *Curr. Opinion Mol. Ther.*, 2001, 3, 239-243; Wengel et al., U.S. Pat. No. 7,053,207, Imanishi et al., U.S. Pat. No. 6,268,490, Imanishi et al. U.S. Pat. No. 6,770,748, Imanishi et al., U.S. RE44,779; Wengel et al., U.S. Pat. No. 6,794,499, Wengel et al., U.S. Pat. No. 6,670,461; Wengel et al., U.S. Pat. No. 7,034,133, Wengel et al., U.S. Pat. No. 8,080,644; Wengel et al., U.S. Pat. No. 8,034,909; Wengel et al., U.S. Pat. No. 8,153,365; Wengel et al., U.S. Pat. No. 7,572,582; and Ramasamy et al., U.S. Pat. No. 6,525,191, Torsten et al., WO 2004/106356, Wengel et al., WO 91999/014226; Seth et al., WO 2007/134181; Seth et al., U.S. Pat. No. 7,547,684; Seth et al., U.S. Pat. No. 7,666,854; Seth et al., U.S. Pat. No. 8,088,746; Seth et al., U.S. Pat. No. 7,750,131; Seth et al., U.S. Pat. No. 8,030,467; Seth et al., U.S. 8,268,980; Seth et al., U.S. Pat. No. 8,546,556; Seth et al., U.S. Pat. No. 8,530,640; Migawa et al., U.S. Pat. No. 9,012,421; Seth et al., U.S. Pat. No. 8,501,805; and U.S. Patent Publication Nos. Allerson et al., US2008/0039618 and Migawa et al., US2015/0191727.

In certain embodiments, bicyclic sugar moieties and nucleosides incorporating such bicyclic sugar moieties are further defined by isomeric configuration. For example, an LNA nucleoside (described herein) may be in the α-L configuration or in the β-D configuration.

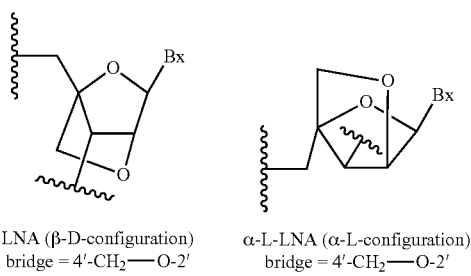

LNA (β-D-configuration)
bridge = 4'-CH$_2$—O-2'

α-L-LNA (α-L-configuration)
bridge = 4'-CH$_2$—O-2'

α-L-methyleneoxy (4'-CH$_2$—O-2') or α-L-LNA bicyclic nucleosides have been incorporated into oligonucleotides that showed antisense activity (Frieden et al., *Nucleic Acids Research*, 2003, 21, 6365-6372). Herein, general descriptions of bicyclic nucleosides include both isomeric configurations. When the positions of specific bicyclic nucleosides (e.g., LNA or cEt) are identified in exemplified embodiments herein, they are in the β-D configuration, unless otherwise specified.

In certain embodiments, modified sugar moieties comprise one or more non-bridging sugar substituent and one or more bridging sugar substituent (e.g., 5'-substituted and 4'-2' bridged sugars).

In certain embodiments, modified sugar moieties are sugar surrogates. In certain such embodiments, the oxygen atom of the sugar moiety is replaced, e.g., with a sulfur, carbon or nitrogen atom. In certain such embodiments, such modified sugar moieties also comprise bridging and/or non-bridging substituents as described herein. For example, certain sugar surrogates comprise a 4'-sulfur atom and a substitution at the 2'-position (see, e.g., Bhat et al., U.S. Pat. No. 7,875,733 and Bhat et al., U.S. Pat. No. 7,939,677) and/or the 5' position.

In certain embodiments, sugar surrogates comprise rings having other than 5 atoms. For example, in certain embodiments, a sugar surrogate comprises a six-membered tetrahydropyran ("THP"). Such tetrahydropyrans may be further modified or substituted. Nucleosides comprising such modified tetrahydropyrans include but are not limited to hexitol nucleic acid ("HNA"), anitol nucleic acid ("ANA"), mannitol nucleic acid ("MNA") (see e.g., Leumann, C J. *Bioorg. & Med. Chem.* 2002, 10, 841-854), fluoro HNA:

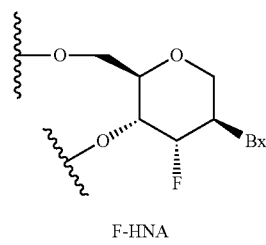

F-HNA ("F-HNA", see e.g., Swayze et al., U.S. Pat. No. 8,088,904; Swayze et al., U.S. Pat. No. 8,440,803; Swayze et al.; and Swayze et al., U.S. Pat. No. 9,005,906, F-HNA can also be referred to as a F-THP or 3'-fluoro tetrahydropyran), and nucleosides comprising additional modified THP compounds having the formula:

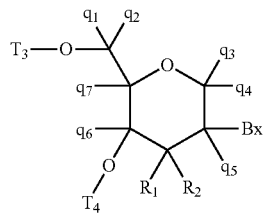

wherein, independently, for each of said modified THP nucleoside: Bx is a nucleobase moiety; T3 and T4 are each, independently, an internucleoside linking group linking the modified THP nucleoside to the remainder of an oligonucleotide or one of T3 and T4 is an internucleoside linking group linking the modified THP nucleoside to the remainder of an oligonucleotide and the other of T3 and 14 is H, a hydroxyl protecting group, a linked conjugate group, or a 5' or 3'-terminal group; $q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from among: hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, modified THP nucleosides are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, modified THP nucleosides are provided wherein one of $R_1$ and $R_2$ is F. In certain embodiments, $R_1$ is F and $R_2$ is H, in certain embodiments, $R_1$ is methoxy and $R_2$ is H, and in certain embodiments, $R_1$ is methoxyethoxy and $R_2$ is H.

In certain embodiments, sugar surrogates comprise rings having more than 5 atoms and more than one heteroatom. For example, nucleosides comprising morpholino sugar moieties and their use in oligonucleotides have been reported (see, e.g., Braasch et al., Biochemistry, 2002, 41, 4503-4510 and Summerton et al., U.S. Pat. No. 5,698,685; Summerton et al., U.S. Pat. No. 5,166,315; Summerton et al., U.S. Pat. No. 5,185,444; and Summerton et al., U.S. Pat. No. 5,034,506). As used here, the term "morpholino" means a sugar surrogate having the following structure:

In certain embodiments, morpholinos may be modified, for example by adding or altering various substituent groups from the above morpholino structure. Such sugar surrogates are referred to herein as "modified morpholinos."

In certain embodiments, sugar surrogates comprise acyclic moieties. Examples of nucleosides and oligonucleotides comprising such acyclic sugar surrogates include but are not limited to: peptide nucleic acid ("PNA"), acyclic butyl nucleic acid (see, e.g., Kumar et al., *Org. Biomol. Chem.*, 2013, 11, 5853-5865), and nucleosides and oligonucleotides described in Manoharan et al., WO2011/133876.

Many other bicyclic and tricyclic sugar and sugar surrogate ring systems are known in the art that can be used in modified nucleosides.

2. Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications can impart nuclease stability, binding affinity or some other beneficial biological property to compounds described herein.

In certain embodiments, compounds described herein comprise modified oligonucleotides. In certain embodiments, modified oligonucleotides comprise one or more nucleoside comprising an unmodified nucleobase. In certain embodiments, modified oligonucleotides comprise one or more nucleoside comprising a modified nucleobase. In certain embodiments, modified oligonucleotides comprise one or more nucleoside that does not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and 0-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl (C≡C—CH3) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyl uracil, universal bases, hydrophobic bases, promiscuous bases, size-expanded bases, and fluorinated bases. Further modified nucleobases include tricyclic pyrimidines, such as 1,3-diazaphenoxazine-2-one, 1,3-diazaphenothiazine-2-one and 9-(2-aminoethoxy)-1,3-diazaphenoxazine-2-one (G-clamp). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in Merigan et al., U.S. Pat. No. 3,687,808, those disclosed in The Concise Encyclopedia Of Polymer Science And Engineering, Kroschwitz, J. I., Ed., John Wiley & Sons, 1990, 858-859; Englisch et al., Angewandte Chemie, International Edition, 1991, 30, 613; Sanghvi, Y. S., Chapter 15, Antisense Research and Applications, Crooke, S. T. and Lebleu, B., Eds., CRC Press, 1993, 273-288; and those disclosed in Chapters 6 and 15, Antisense Drug Technology, Crooke S. T., Ed., CRC Press, 2008, 163-166 and 442-443.

Publications that teach the preparation of certain of the above noted modified nucleobases as well as other modified nucleobases include without limitation, Manoharan et al., US2003/0158403, Manoharan et al., US2003/0175906; Dinh et al., U.S. Pat. No. 4,845,205; Spielvogel et al., U.S. Pat. No. 5,130,302; Rogers et al., U.S. Pat. No. 5,134,066; Bischofberger et al., U.S. Pat. No. 5,175,273; Urdea et al., U.S. Pat. No. 5,367,066; Benner et al., U.S. Pat. No. 5,432,272; Matteucci et al., U.S. Pat. No. 5,434,257; Gmeiner et al., U.S. Pat. No. 5,457,187; Cook et al., U.S. Pat. No. 5,459,255; Froehler et al., U.S. Pat. No. 5,484,908; Matteucci et al., U.S. Pat. No. 5,502,177; Hawkins et al., U.S. Pat. No. 5,525,711; Haralambidis et al., U.S. Pat. No. 5,552,540; Cook et al., U.S. Pat. No. 5,587,469; Froehler et al., U.S. Pat. No. 5,594,121; Switzer et al., U.S. Pat. No. 5,596,091; Cook et al., U.S. Pat. No. 5,614,617; Froehler et al., U.S. Pat. No. 5,645,985; Cook et al., U.S. Pat. No. 5,681,941; Cook et al., U.S. Pat. No. 5,811,534; Cook et al., U.S. Pat. No. 5,750,692; Cook et al., U.S. Pat. No. 5,948,903; Cook et al., U.S. Pat. No. 5,587,470; Cook et al., U.S. Pat. No. 5,457,191; Matteucci et al., U.S. Pat. No. 5,763,588; Froehler et al., U.S. Pat. No. 5,830,653; Cook et al., U.S. Pat. No. 5,808,027; Cook et al., U.S. Pat. No. 6,166,199; and Matteucci et al., U.S. Pat. No. 6,005,096.

In certain embodiments, compounds targeted to a SCN2A nucleic acid comprise one or more modified nucleobases. In certain embodiments, the modified nucleobase is 5-methylcytosine. In certain embodiments, each cytosine is a 5-methylcytosine.

Modified Internucleoside Linkages

The naturally occurring internucleoside linkage of RNA and DNA is a 3' to 5' phosphodiester linkage. In certain embodiments, compounds described herein having one or more modified, i.e., non-naturally occurring, internucleoside linkages are often selected over compounds having naturally occurring internucleoside linkages because of desirable properties such as, for example, enhanced cellular uptake, enhanced affinity for target nucleic acids, and increased stability in the presence of nucleases.

In certain embodiments, compounds targeted to a SCN2A nucleic acid comprise one or more modified internucleoside linkages. In certain embodiments, the modified internucleoside linkages are phosphorothioate linkages. In certain embodiments, each internucleoside linkage of the compound is a phosphorothioate internucleoside linkage.

In certain embodiments, compounds described herein comprise oligonucleotides. Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, nucleosides of modified oligonucleotides may be linked together using any internucleoside linkage. The two main classes of internucleoside linking groups are defined by the presence or absence of a phosphorus atom. Representative phosphorus-containing internucleoside linkages include but are not limited to phosphates, which contain a phosphodiester bond ("P═O") (also referred to as unmodified or naturally occurring linkages), phosphotriesters, methylphosphonates, phosphoramidates, and phosphorothioates ("P=S"), and phosphorodithioates ("HS—P=S"). Representative non-phosphorus containing internucleoside linking groups include but are not limited to methylenemethylimino (—CH2-N(CH3)-O—CH2-), thiodiester, thionocarbamate (—O—C(=O)(NH)—S—); siloxane (—O—SiH2-O—); and N,N'-dimethylhydrazine (—CH2-N(CH3)-N(CH3)-). Modified internucleoside linkages, compared to naturally occurring phosphate linkages, can be used to alter, typically increase, nuclease resistance of the oligonucleotide. In certain embodiments, internucleoside linkages having a chiral atom can be prepared as a racemic mixture, or as separate enantiomers. Representative chiral internucleoside linkages include but are not limited to alkylphosphonates and phosphorothioates. Methods of preparation of phosphorous-containing and non-phosphorous-containing internucleoside linkages are well known to those skilled in the art.

Neutral internucleoside linkages include, without limitation, phosphotriesters, methylphosphonates, MMI (3'-CH2-N(CH3)-O-5'), amide-3 (3'-CH2-C(=O)—N(H)-5'), amide-4 (3'-CH2-N(H)—C(=O)-5'), formacetal (3'-O—CH2-O-5'), methoxypropyl, and thioformacetal (3'-S—CH2-O-5'). Further neutral internucleoside linkages include nonionic linkages comprising siloxane (dialkylsiloxane), carboxylate ester, carboxamide, sulfide, sulfonate ester and amides (See for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and CH2 component parts.

In certain embodiments, oligonucleotides comprise modified internucleoside linkages arranged along the oligonucleotide or region thereof in a defined pattern or modified internucleoside linkage motif. In certain embodiments, internucleoside linkages are arranged in a gapped motif. In such embodiments, the internucleoside linkages in each of two wing regions are different from the internucleoside linkages in the gap region. In certain embodiments the internucleoside linkages in the wings are phosphodiester and the internucleoside linkages in the gap are phosphorothioate. The nucleoside motif is independently selected, so such oligonucleotides having a gapped internucleoside linkage motif may or may not have a gapped nucleoside motif and if it does have a gapped nucleoside motif, the wing and gap lengths may or may not be the same.

In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

In certain embodiments, oligonucleotides comprise one or more methylphosphonate linkages. In certain embodiments, oligonucleotides having a gapmer nucleoside motif comprise a linkage motif comprising all phosphorothioate linkages except for one or two methylphosponate linkages. In certain embodiments, one methylphosphonate linkage is in the central gap of an oligonucleotide having a gapmer nucleoside motif.

In certain embodiments, it is desirable to arrange the number of phosphorothioate internucleoside linkages and phosphodiester internucleoside linkages to maintain nuclease resistance. In certain embodiments, it is desirable to arrange the number and position of phosphorothioate internucleoside linkages and the number and position of phosphodiester internucleoside linkages to maintain nuclease resistance. In certain embodiments, the number of phosphorothioate internucleoside linkages may be decreased and the number of phosphodiester internucleoside linkages may be increased. In certain embodiments, the number of phosphorothioate internucleoside linkages may be decreased and the number of phosphodiester internucleoside linkages may be increased while still maintaining nuclease resistance. In certain embodiments it is desirable to decrease the number of phosphorothioate internucleoside linkages while retaining nuclease resistance. In certain embodiments it is desirable to increase the number of phosphodiester internucleoside linkages while retaining nuclease resistance.

B. Certain Motifs

In certain embodiments, compounds described herein comprise oligonucleotides. Oligonucleotides can have a motif, e.g., a pattern of unmodified and/or modified sugar moieties, nucleobases, and/or internucleoside linkages. In certain embodiments, modified oligonucleotides comprise one or more modified nucleoside comprising a modified sugar. In certain embodiments, modified oligonucleotides comprise one or more modified nucleosides comprising a modified nucleobase. In certain embodiments, modified oligonucleotides comprise one or more modified internucleoside linkage. In such embodiments, the modified, unmodified, and differently modified sugar moieties, nucleobases, and/or internucleoside linkages of a modified oligonucleotide define a pattern or motif. In certain embodiments, the patterns of sugar moieties, nucleobases, and internucleoside linkages are each independent of one another. Thus, a modified oligonucleotide may be described by its sugar motif, nucleobase motif and/or internucleoside linkage motif (as used herein, nucleobase motif describes the modifications to the nucleobases independent of the sequence of nucleobases).

1. Certain Sugar Motifs

In certain embodiments, compounds described herein comprise oligonucleotides. In certain embodiments, oligonucleotides comprise one or more type of modified sugar and/or unmodified sugar moiety arranged along the oligonucleotide or region thereof in a defined pattern or sugar motif. In certain instances, such sugar motifs include but are not limited to any of the sugar modifications discussed herein.

In certain embodiments, modified oligonucleotides comprise or consist of a region having a gapmer motif, which comprises two external regions or "wings" and a central or internal region or "gap." The three regions of a gapmer motif (the 5'-wing, the gap, and the 3'-wing) form a contiguous sequence of nucleosides wherein at least some of the sugar moieties of the nucleosides of each of the wings differ from at least some of the sugar moieties of the nucleosides of the gap. Specifically, at least the sugar moieties of the nucleosides of each wing that are closest to the gap (the 3'-most nucleoside of the 5'-wing and the 5'-most nucleoside of the 3'-wing) differ from the sugar moiety of the neighboring gap nucleosides, thus defining the boundary between the wings and the gap (i.e., the wing/gap junction). In certain embodiments, the sugar moieties within the gap are the same as one another. In certain embodiments, the gap includes one or more nucleoside having a sugar moiety that differs from the sugar moiety of one or more other nucleosides of the gap. In certain embodiments, the sugar motifs of the two wings are the same as one another (symmetric gapmer). In certain embodiments, the sugar motif of the 5'-wing differs from the sugar motif of the 3'-wing (asymmetric gapmer).

In certain embodiments, the wings of a gapmer comprise 1-5 nucleosides. In certain embodiments, the wings of a gapmer comprise 2-5 nucleosides. In certain embodiments, the wings of a gapmer comprise 3-5 nucleosides. In certain embodiments, the nucleosides of a gapmer are all modified nucleosides.

In certain embodiments, the gap of a gapmer comprises 7-12 nucleosides. In certain embodiments, the gap of a gapmer comprises 7-10 nucleosides. In certain embodiments, the gap of a gapmer comprises 8-10 nucleosides. In certain embodiments, the gap of a gapmer comprises 10 nucleosides. In certain embodiment, each nucleoside of the gap of a gapmer is an unmodified 2'-deoxy nucleoside.

In certain embodiments, the gapmer is a deoxy gapmer. In such embodiments, the nucleosides on the gap side of each wing/gap junction are unmodified 2'-deoxy nucleosides and the nucleosides on the wing sides of each wing/gap junction are modified nucleosides. In certain such embodiments, each nucleoside of the gap is an unmodified 2'-deoxy nucleoside. In certain such embodiments, each nucleoside of each wing is a modified nucleoside.

In certain embodiments, a modified oligonucleotide has a fully modified sugar motif wherein each nucleoside of the modified oligonucleotide comprises a modified sugar moiety. In certain embodiments, modified oligonucleotides comprise or consist of a region having a fully modified sugar motif wherein each nucleoside of the region comprises a modified sugar moiety. In certain embodiments, modified oligonucleotides comprise or consist of a region having a fully modified sugar motif, wherein each nucleoside within the fully modified region comprises the same modified sugar moiety, referred to herein as a uniformly modified sugar motif. In certain embodiments, a fully modified oligonucleotide is a uniformly modified oligonucleotide. In certain embodiments, each nucleoside of a uniformly modified comprises the same 2'-modification.

2. Certain Nucleobase Motifs

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments the block is within 3 nucleosides of the 3'-end of the oligonucleotide. In certain embodiments, the block is at the 5'-end of the oligonucleotide. In certain embodiments the block is within 3 nucleosides of the 5'-end of the oligonucleotide.

In certain embodiments, oligonucleotides having a gapmer motif comprise a nucleoside comprising a modified nucleobase. In certain such embodiments, one nucleoside comprising a modified nucleobase is in the central gap of an oligonucleotide having a gapmer motif. In certain such embodiments, the sugar moiety of said nucleoside is a 2'-deoxyribosyl moiety. In certain embodiments, the modified nucleobase is selected from: a 2-thiopyrimidine and a 5-propynepyrimidine.

3. Certain Internucleoside Linkage Motifs

In certain embodiments, compounds described herein comprise oligonucleotides. In certain embodiments, oligonucleotides comprise modified and/or unmodified internucleoside linkages arranged along the oligonucleotide or region thereof in a defined pattern or motif. In certain embodiments, essentially each internucleoside linking group is a phosphate internucleoside linkage (P=O). In certain embodiments, each internucleoside linking group of a modified oligonucleotide is a phosphorothioate (P=S). In certain embodiments, each internucleoside linking group of a modified oligonucleotide is independently selected from a phosphorothioate and phosphate internucleoside linkage. In certain embodiments, the sugar motif of a modified oligonucleotide is a gapmer and the internucleoside linkages within the gap are all modified. In certain such embodiments, some or all of the internucleoside linkages in the wings are unmodified phosphate linkages. In certain embodiments, the terminal internucleoside linkages are modified.

C. Certain Modified Oligonucleotides

In certain embodiments, compounds described herein comprise modified oligonucleotides. In certain embodiments, the above modifications (sugar, nucleobase, internucleoside linkage) are incorporated into a modified oligonucleotide. In certain embodiments, modified oligonucleotides are characterized by their modification, motifs, and overall lengths. In certain embodiments, such parameters are each independent of one another. Thus, unless otherwise indicated, each internucleoside linkage of an oligonucleotide having a gapmer sugar motif may be modified or unmodified and may or may not follow the gapmer modification pattern of the sugar modifications. For example, the internucleoside linkages within the wing regions of a sugar gapmer may be the same or different from one another and may be the same or different from the internucleoside linkages of the gap region of the sugar motif. Likewise, such gapmer oligonucleotides may comprise one or more modified nucleobase independent of the gapmer pattern of the sugar modifications. Furthermore, in certain instances, an oligonucleotide is described by an overall length or range and by lengths or length ranges of two or more regions (e.g., a regions of nucleosides having specified sugar modifications), in such circumstances it may be possible to select numbers for each range that result in an oligonucleotide having an overall length falling outside the specified range. In such circumstances, both elements must be satisfied. For example, in certain embodiments, a modified oligonucleotide consists of 15-20 linked nucleosides and has a sugar motif consisting of three regions, A, B, and C, wherein region A consists of 2-6 linked nucleosides having a specified sugar motif, region B consists of 6-10 linked nucleosides having a specified sugar motif, and region C consists of 2-6 linked nucleosides having a specified sugar motif. Such embodiments do not include modified oligonucleotides where A and C each consist of 6 linked nucleosides and B consists of 10 linked nucleosides (even though those numbers of nucleosides are permitted within the requirements for A, B, and C) because the overall length of such oligonucleotide is 22, which exceeds the upper limit of the overall length of the modified oligonucleotide (20). Herein, if a description of an oligonucleotide is silent with respect to one or more parameter, such parameter is not limited. Thus, a modified oligonucleotide described only as having a gapmer sugar motif without further description may have any length, internucleoside linkage motif, and nucleobase motif. Unless otherwise indicated, all modifications are independent of nucleobase sequence.

Compositions and Methods for Formulating Pharmaceutical Compositions

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

In certain embodiments, the present invention provides pharmaceutical compositions comprising one or more compounds or a salt thereof. In certain embodiments, the compounds are antisense compounds or oligomeric compounds. In certain embodiments, the compounds comprise or consist of a modified oligonucleotide. In certain such embodiments, the pharmaceutical composition comprises a suitable pharmaceutically acceptable diluent or carrier. In certain embodiments, a pharmaceutical composition comprises a sterile saline solution and one or more compound. In certain embodiments, such pharmaceutical composition consists of a sterile saline solution and one or more compound. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compound and phosphate-buffered saline (PBS). In certain embodiments, a pharmaceutical composition consists of one or more compound and sterile PBS. In certain embodiments, the sterile PBS is pharmaceutical grade PBS. Compositions and methods for the formulation of pharmaceutical compositions are dependent upon a number of criteria, including, but not limited to, route of administration, extent of disease, or dose to be administered.

A compound described herein targeted to a SCN2A nucleic acid can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to a SCN2A nucleic acid and a pharmaceutically acceptable diluent. In certain embodiments, the pharmaceutically acceptable diluent is water. In certain embodiments, the compound comprises or consists of a modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense compounds or oligomeric compounds. In certain embodiments, the compound comprises or consists of a modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of a compound which are cleaved by endogenous nucleases within the body, to form the active compound.

In certain embodiments, the compounds or compositions further comprise a pharmaceutically acceptable carrier or diluent.

Advantages of Certain Embodiments

Provided herein, for the first time, are methods and compositions for the modulation of a SCN2A nucleic acid that can treat, delay, prevent and/or ameliorate an SCN1A-related disease or condition (e.g., Dravet syndrome), or a physiological marker thereof. In a particular embodiment, for the first time, SCN2A inhibitors (e.g., oligonucleotides targeting a nucleic acid encoding SCN2A) are provided for decreasing seizures, decreasing myoclonus or muscle spasms, alleviating difficulty in walking, reducing, preventing the onset of or treating dementia, alleviating difficulties in speech, reducing or preventing the onset of visual hallucinations, treating, reducing or preventing the onset of progressive neurologic degeneration, reducing ataxia, or a combination thereof in a subject having an SCN1A-related disease or condition (e.g., Dravet syndrome).

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: SCN2A mRNA was Reduced by LNAs

LNAs were dissolved to 10 µg/µl with sterile distilled water and stored at −30° C. until use. The sequences of LNAs used are shown below in Tables 1 and 2.

TABLE 1

ASO sequences

| RGCN# | Sequence in gene | Position in NM_001099298 | Intron/Exon | Human cross-reactive | ASO sequence (LNA) |
|---|---|---|---|---|---|
| ASO 1 | AAAGCTAAGAGACCCA (SEQ ID NO: 1) | 1907 | Exon | Y | TGGGTCTCTTAGCTTT (SEQ ID NO: 4) |
| ASO 2 | AGATTGCATTTTCACC (SEQ ID NO: 2) | 21683 | Intron | N | GGTGAAAATGCAATCT (SEQ ID NO: 5) |
| ASO 3 | GGCAATACTTCCCAAC (SEQ ID NO: 3) | 38752 | Intron | N | GTTGGGAAGTATTGCC (SEQ ID NO: 6) |

TABLE 2

ASO sequences Exiqon nomenclature

| RGCN# | Exiqon Nomenclature |
|---|---|
| ASO 1 | +T*+a*+G*+G*T*C*T*C*T*T*A*G*+C*+T*+T*+T (SEQ ID NO: 4) |
| ASO 2 | +G*+G*+T*+G*A*A*A*A*T*G*C*A*+A*+T*+C*+T (SEQ ID NO: 5) |
| ASO 3 | +G*+T*+T*+G*G*G*A*A*G*T*A*T*+T*+G*+C*+C (SEQ ID NO: 6) |

Neonatal Intracerebroventricular (ICV) Injection

All studies were carried out in accordance with the Guide for the Care and Use of Laboratory Animals and were approved by the Florey Institute Animal Ethics Committee. Pregnant ICR mice carrying pups heterozygous for the Scn2a R1882Q mutation were generated by Cyagen. Mice were maintained in a temperature-controlled room, with a 12-hour light on/off cycle and free access to food and liquid.

Before injection, pups (P2) were visually inspected to ensure milk spot was present. Cryoanesthesia was induced by placing the pups into a small plastic container surrounded by crushed ice for 4-5 minutes and toe-pinch response was used to determine the depth of anesthesia. LNA (10 µg/µl) was loaded into a 10 µl syringe with a 32 G needle (Hamilton). The skin surface of the pup was sterilized by an 80% ethanol swab, and injection site was labelled with a marker at a location approximately 0.7-1.0 mm lateral to the sagittal suture and 0.7-1.0 mm rostral from lambda. The needle was inserted 2 mm below skin surface, at an angle perpendicular to the skull surface. LNA (20 µg) at a volume of 2 µl was slowly injected into the right ventricle. To recover, mice were kept on the heat block (32 Celsius) for 5-10 mins until movement was observed. Before returning to home cage, pups were rubbed in beddings to minimize the risk of infanticide.

The right cerebral hemisphere of LNA-treated mice were harvested at P15 and P35, and were then snap-frozen with liquid nitrogen. Total RNA was isolated using TRIzol reagent (ThermoFisher Scientific). 1 ml of TRIzol was used per hemisphere for the initial homogenization and the RNA isolation was performed according to the manufacturer's protocol. Afterwards, up to 20 µg of total RNA per sample were treated with 1 µl of DNase (DNA-free DNase treatment and removal kit; ThermoFisher Scientific) in a 50 µl reaction following the manufacturer's instructions; DNase was subsequently removed using the supplied inactivation reagent (DNA-free DNase treatment and removal kit; ThermoFisher Scientific). To generate cDNA, 500 ng of total RNA per sample were reverse transcribed by M-MLV reverse transcriptase using oligo(dT)15 primers (both Promega) according to the manufacturer's protocols. Subsequently, 20 ng of cDNA per sample were used as template in quantitative real time PCRs (qRT-PCRs). qRT-PCR reactions were prepared using the GoTaq qPCR MasterMix (Promega) following the manufacturer's instructions, and reactions were performed in MicroAmp Fast-Optical 96-well reaction plates (ThermoFisher Scientific) on the ViiA 7 system (ThermoFisher Scientific). During the qRT-PCR run, an initial pre-incubation for 10 min at 95° C. was followed by 40 amplification cycles (95° C. for 15 s, 60° C. for 60 s). Finally, a melting point analysis was performed (95° C. for 15 s, 60° C. for 60 s, heating to 95° C. at a rate of 0.05° C./s) to determine the melting temperatures of the amplified products. The primer sequences (5'-3') were: TGCTGTGCGGAAATCTGCC (SCN2A forward primer) (SEQ ID NO: 7); CGGATGCT-CAAGAGAGACTGG (SCN2A reverse primer) (SEQ ID NO: 8); GAGGTGCTGCTGATGTGC (RPL32 forward primer) (SEQ ID NO: 9); GGCGTTGGGATTGGTGACT (RPL32 reverse primer) (SEQ ID NO: 10). qRT-PCR data was analysed using the QuantStudio Real Time PCR software v1.3 (ThermoFisher Scientific). For quantitative expression analysis, the expression of SCN2A was normalized to the expression of the housekeeping gene RPL32 ($2^{\Delta CT}$ method; Pfaffl et al., Nucl. Acids. Res. 29(9): e45, 2001). The normalized expression of SCN2A in ASO-treated mice was then normalized to the expression of SCN2A in age-matched untreated controls ($2^{\Delta\Delta CT}$).

Figure 1B:
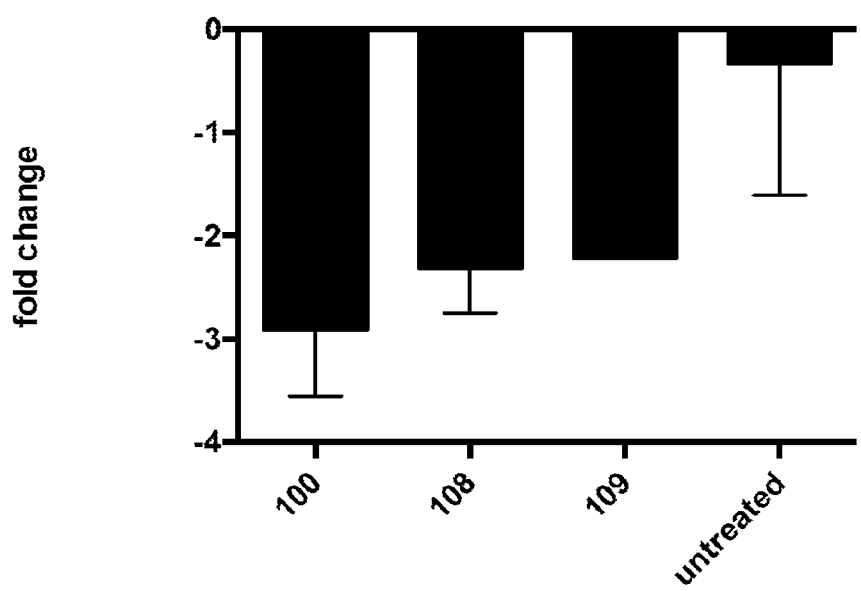

All three LNAs (ASO 1, ASO 2, and ASO 3) reduced Scn2a mRNA level by 2-3 fold 13 days post-injection (FIG. 1A). A similar level of reduction was observed at P35 (FIG. 1B), indicating that LNAs were stable in CSF and were efficacious in downregulating Scn2a mRNA for a minimum of 1 month.

Example 2: SCN2A ASO Assessment of Survival and Seizures in SCN1A Heterozygous Mice Background The SCN1A R1407X mouse model (Scn1a RX) closely mirrors key disease features of an early onset, severe epilepsy known as Dravet syndrome. Mice heterozygous for the R1407X mutation have premature death and spontaneous seizures. The Scn1a gene encodes for a voltage gated sodium channel, Nav1.1, which predominantly expresses in inhibitory neurons. Electrophysiological analyses revealed that neurons expressing R1407X cannot sustain high frequency action potential firing, thus resulting in dis-inhibition and consequently, hyper excitability in the brain. Therefore, strategies that can reduce general hyper excitability in the brain may be therapeutic for Dravet syndrome. A key regulator of brain excitability during early development is another voltage gated sodium channel isoform, Nav1.2, encoded by the SCN2A gene.

A method to reduce Nav1.2 function is to target the SCN2A gene using antisense oligonucleotides (ASOs). ASOs are single-stranded DNA/RNA oligonucleotides that were designed to control the gene expression of interest. ASOs specifically designed to downregulate the mouse SCN1A gene were applied into the SCN1A RX mouse model and efficacy evaluated by survival, number of spontaneous seizure and electroencephalogram (EEG).

Methods

Quantitative Gene Expression Analysis (RT-qPCR)

Total RNA was isolated from mouse brain tissue using the Trizol reagent according to manufacturer's protocols (Thermofisher, USA). Contaminating genomic DNA was removed with DNAse treatment (DNA-free Reagents, Ambion/Life Technologies, USA). Mouse (F: TGCTGTGCGGAAATCTGCC (SEQ ID NO: 7), R: CGGATGCTCAAGAGAGACTGG (SEQ ID NO: 8)) SCN2A targeting primers were designed to span introns to discriminate between amplification of genomic DNA and cDNA. For RT-qPCR, oligo-dT primed cDNA was synthesized from 500 ng of total RNA using Murine Moloney Leukaemia Virus Reverse Transcriptase (Promega, USA). RT-qPCR on the ViiA 7 Real-Time PCR System using GoTaq qPCR master mix (Promega, USA) was performed according to the manufacturer's protocols. Relative gene expression values were obtained by normalization to the reference gene RPL32 using the 2DDCt method.

Neonatal Intracerebroventricular Injection

SCN1A RX pups were administered with 5 µg of mouse SCN2A antisense oligonucleotides (mScn2a ASO) or the negative control, 50 µg of scrambled ASO, on postnatal day (P) 1 via the intracerebroventricular (icv) route. Pups were cryo-anaesthetised, then a syringe needle (32G, Hamilton) loaded with ASO was inserted midway between lamda and right eye. The injection depth was 2 mm below skin surface and a total of 2 µl of mScn2a ASO was administered to the right ventricle.

Seizure Monitoring

SCN1A RX mice were grouped housed in home cage and placed under 24-hour video monitoring from P21 to P28. Videos were reviewed by two experimenters, and seizures over Racine score 4 were noted. The averaged group seizure was calculated by dividing the total number of seizures per treatment group over the number of mice in the treatment group.

Electroencephalography (EEG)

SCN1A RX mice (P30-35) were anaesthetised with 1-3% isoflurane. Mice were placed in a stereotaxic apparatus (Kopf) with the skull surface horizontal between lambda and bregma. Four epidural electrodes were placed on the brain surface and secured in place with dental cement. Mice were recovered for 4-7 days before EEG recording. Brain cortical activity was monitored for 24 hours (Pinnacle Technology). During recording, mice could move freely in the cage with food and water ad libitum.

Results

Reduction of Scn2a mRNA by ASO Administration

Figure 2:
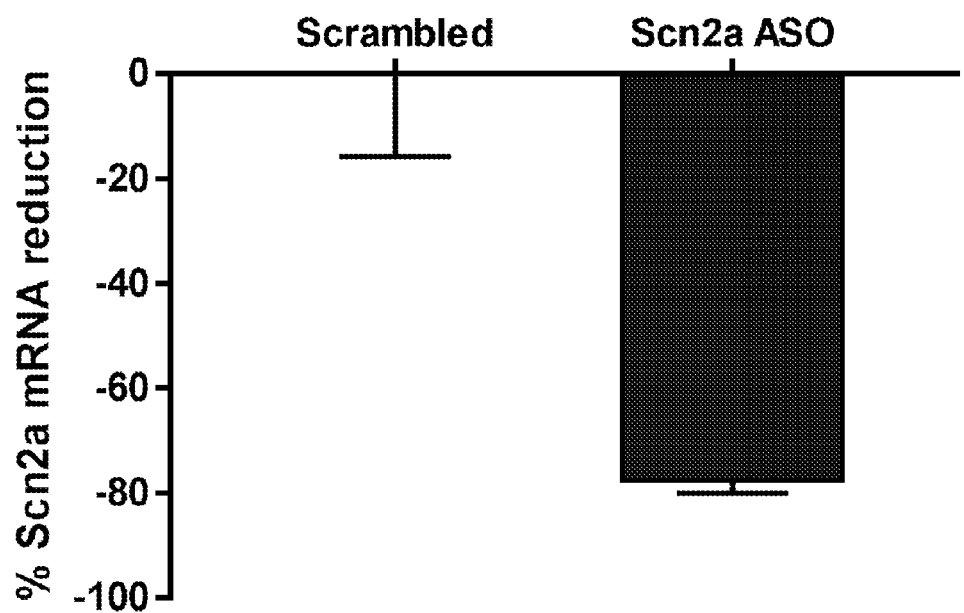
FIG. 2 is a graph showing percentage of Scn2a mRNA reduction normalised to untreated age matched Scn1a RX heterozygous mice. The mRNA was measured on P15. N=3 brain samples per treatment group.
Figure 3:
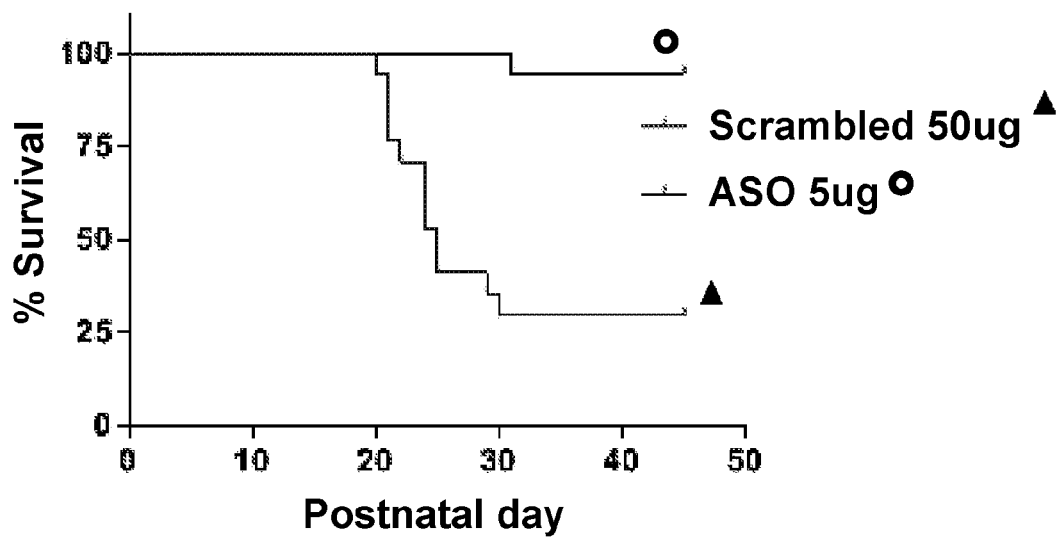
FIG. 3 is a graph showing % survival in mice heterozygous for Scn1a following injection with Scn2a downregulatory ASO (5 μg) or scrambled ASO (50 μg). All mice were injected on P1 and tracked for 45 days.
Figure 4A:
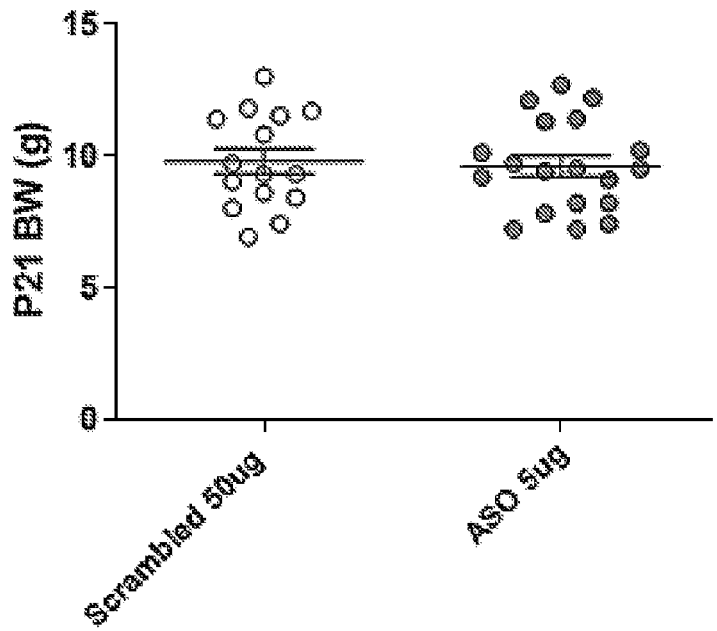
FIG. 4A is a graph showing body weight of scrambled or mScn2a ASO treated Scn1a RX mice on P21. N=15 for scrambled, and N=18 for ASO.
Figure 4B:
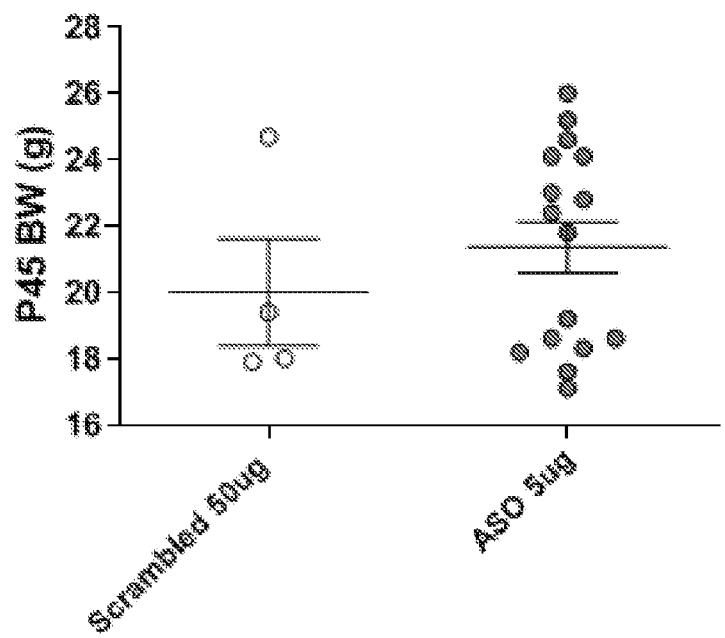
FIG. 4B is a graph showing body weight of scrambled or mScn2a ASO treated Scn1a RX mice on P45. N=15 for scrambled, and N=18 for ASO.

The mScn2a ASO (5 µg) or scrambled ASO (50 µg) were injected into the right ventricle of Scn1a RX pups on P1. The mRNA level of Scn2a was assessed 14 days post ASO administration. As expected, the scrambled ASO did not affect Scn2a mRNA expression. Brains collected from mScn2a ASO treated mice showed 78.15±1.87% reduction in Scn2a mRNA level (FIG. 2). In scrambled ASO treated Scn1a RX mice, survival was 76.47% on P21. No death was observed by P21 in mScn2a ASO treated Scn1a RX mice (FIG. 3). The body weight was similar between scrambled ASO and mScn2a ASO treated Scn1a RX mice on P21 and P45 (FIGS. 4A-4B). By experimental endpoint (P45), the survival rate was 29.41% and 94.44% for scrambled and mScn2a ASO respectively.

ASO Improves Seizure Phenotype of the Survival of Scn1a RX Mouse Model

Figure 5:
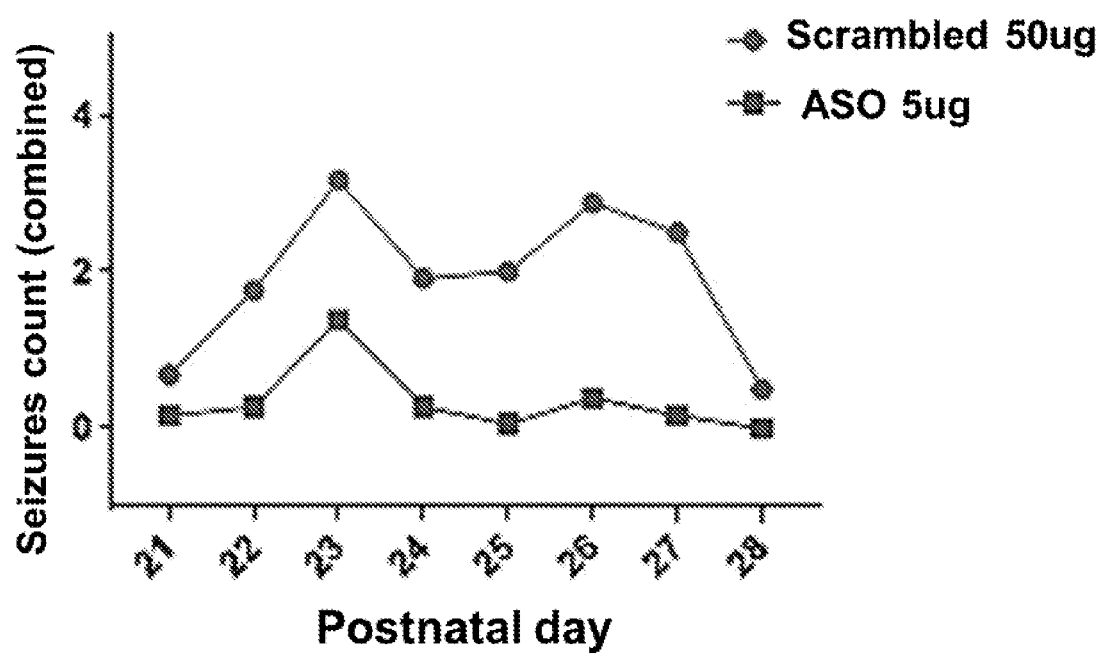
FIG. 5 is a graph showing number of seizures in mice heterozygous for Scn1a following injection with Scn2a downregulatory ASO (5 μg; n=9) or scrambled ASO (50 μg; n=17). All mice were injected on P1.

Frequent seizure is a debilitating feature of Dravet syndrome, thus seizure episode is a critical marker for therapeutic efficacy. Scn1a RX mice were group housed according to their treatment and placed under 24-hour video monitoring from P21 to P28 (FIG. 5). Videos were reviewed and seizures above Racine score 4 was noted. Spontaneous seizure was significantly reduced by 5 µg mScn2a ASO in comparison to scrambled ASO treated Scn1a RX mice.

Outcomes form this study demonstrated the remarkable therapeutic efficacy of mScn2a ASO in a mouse model of Dravet Syndrome. The lifespan of the disease mouse model was extended, and spontaneous seizure phenotype was significantly improved.

Example 3: In Vitro Decrease in Translation of SCN2A with an SCN2A ASO

Human SH-SY5Y cells that naturally express SCN2A are maintained and incubated in proper cell culture. The SH-SY5Y cells are treated with a 20mer antisense oligonucleotide targeting the SCN2A gene. RNA and protein levels are measured in separate concentration response and time course experiments. RNA levels can be measured through northern blotting, RT-PCR, and/or quantitative PCR analysis. Protein levels are measured through western blotting analysis.

Example 4: Treatment of Dravet Syndrome by Administration of an SCN2A ASO

A human patient with Dravet syndrome is selected for ASO treatment. A 20mer antisense oligonucleotide targeting SCN2A mRNA is synthesized with phosphorothioate linkages throughout and 2MOE modifications on all sugar moieties. The ASO is dissolved in a suitable excipient compatible with administration to a human. A solution containing the dissolved ASO is injected into neuronal cells of the patient such that the ASO solution interacts with the affected neuronal cells. The ASO transfects the neuronal cells and alters the translation of SCN2A in the target cells, leading to a decrease in SCN2A protein. A quantitative assay (e.g., western blot) is performed to measure the decrease in SCN2A protein. Immunohistochemistry and immunogold staining is used to directly visualize the reduction of SCN2A in neuronal cells. The patient undergoes extensive regular testing to measure a reduction of symptoms associated with Dravet syndrome following administration of the ASO treatment.

Example 5: Prevention of Dravet Syndrome by Administration of an SCN2A ASO

A human patient with an SCN1A mutation, a genetic marker for Dravet syndrome, is selected for ASO treatment. A 20mer antisense oligonucleotide targeting SCN2A mRNA is synthesized with phosphorothioate linkages throughout and 2MOE modifications on all sugar moieties. The ASO is dissolved in a suitable excipient compatible with administration to a human. A solution containing the dissolved ASO is injected into the neuronal cells of the patient such that the ASO solution interacts with the affected neuronal cells. The ASO transfects the neuronal cells and alters the translation of SCN2A in the target cells, leading to a decrease in SCN2A protein. A quantitative assay (e.g., western blot) is performed to measure the decrease in SCN2A protein. Immunohistochemistry and immunogold staining is used to directly visualize the reduction of SCN2A in neuronal cells. The patient undergoes extensive regular testing to observe whether onset of symptoms associated with Dravet syndrome onset following administration of the ASO treatment.

The invention claimed is:

1. A method of treating an SCN1A encephalopathy in a subject in need thereof, the method comprising administering to the subject a composition comprising a single-stranded oligonucleotide, wherein the single-stranded oligonucleotide is 10-80 nucleosides in length and has a nucleobase sequence comprising a portion of 10 contiguous nucleobases having at least 80% complementarity to an equal length portion of a target region of a pre-mRNA transcript or an mRNA transcript of a human SCN2A gene, in an amount and for a duration sufficient to treat the SCN1A encephalopathy, wherein the subject has a loss-of-function mutation in SCN1A, and wherein the single-stranded oligonucleotide is selective for SCN2A pre-mRNA or mRNA over SCN1A pre-mRNA or mRNA.

2. The method of claim 1, wherein the single-stranded oligonucleotide comprises a nucleobase sequence complementary to a portion of SCN2A mRNA that encodes the amino acid sequence of SEQ ID NO: 11 or comprises the nucleobase sequence of SEQ ID NO: 12.

3. The method of claim 1, wherein the single-stranded oligonucleotide comprises one or more modified sugars, one or more modified internucleoside linkages, and/or one or more modified nucleobases.

4. The method of claim 3, wherein each of the one or more modified sugars is independently selected from the group consisting of a bicyclic sugar, a 2'-O methoxyethyl (2MOE) modified sugar, a 2'-O-methoxy (2-OMe) modified sugar, a 2'-methoxy modified sugar, a 2'-O-alkyl modified sugar, a constrained ethyl (cEt) modified sugar, a locked sugar, and an unlocked sugar.

5. The method of claim 3, wherein each of the one or more modified internucleoside linkages comprises a modified phosphate, wherein each of the one or more modified phosphates is independently selected from the group consisting of a phosphorothioate, a phosphorodithioate, a phosphoramidate, a phosphorodiamidate, a thiophosphoramidate, a thiophosphorodiamidate, a methyl phosphonate, a phosphoromorpholidate, and a phosphoropiperazidate.

6. The method of claim 3, wherein each of the one or more modified nucleobases is selected from the group consisting of 5-methylcytosine, 5-hydroxymethyl cytosine, xanthine, hypoxanthine, 2-aminoadenine, 6-methyladenine, 6-methylguanine, 2-propyladenine, 2-propylguanine, 2-thiouracil, 2-thiothymine, 2-thiocytosine, 5-halouracil, 5-halocytosine, 5-propynyluracil, 5-propynylcytosine, 6-azouracil, 6-azocytosine, 6-azothymine, 5-uracil (pseudouracil), 4-thiouracil, 8-haloadenine, 8-aminoadenine, 8-thioladenine, 8-thioalkyladenine, 8-hydroxyladenine, 8-haloguanine, 8-aminoguanine, 8-thiolguanine, 8-thioalkylguanine, 8-hydroxylguanine, 5-bromouracil, 5-trifluoromethyluracil, 5-bromocytosine, 5-trifluoromethy!cytosine, 7-methylguanine, 7-methyladenine, 2-fluoroadenine, 8-azaguanine, 8-azaadenine, 7-deazaguanine, 7-deazaadenine, 3-deazaguanine, and 3-deazaadenine.

7. The method of claim 3, wherein the single-stranded oligonucleotide comprises:
- a gap segment consisting of linked deoxynucleosides;
- a 5' wing segment consisting of linked nucleosides; and
- a 3' wing segment consisting of linked nucleosides;
- wherein the gap segment is positioned immediately adjacent to and between the 5' wing segment and the 3' wing segment; and
- wherein each nucleoside of each wing segment comprises a modified sugar.

8. The method of claim 1, wherein the single-stranded oligonucleotide consists of 12 to 40 nucleobases.

9. The method of claim 1, wherein the method provides inhibition of the expression of SCN2A in neuronal cells in the subject.

10. The method of claim 1, wherein the SCN1A encephalopathy is selected from the group consisting of epilepsy, generalized epilepsy with febrile seizures, familial febrile seizures, early infantile epileptic encephalopathy 6, and Dravet syndrome.

11. The method of claim 10, wherein the SCN1A encephalopathy is Dravet syndrome.

12. The method of claim 1, wherein the composition is administered intrathecally, intramedullary, or intracerebroventricularly.

13. The method of claim 1, wherein the method reduces one or more symptoms of the SCN1A encephalopathy.

14. The method of claim 13, wherein the one or more symptoms of the SCN1A encephalopathy is selected from the group consisting of prolonged seizures, frequent seizures, behavioral and developmental delays, movement and balance issues, orthopedic conditions, delayed language and speech issues, growth and nutrition issues, sleeping difficulties, chronic infection, sensory integration disorder, disruption of the autonomic nervous system, migraines, and sweating.

* * * * *